(12) United States Patent
Marshik-Geurts et al.

(10) Patent No.: US 7,689,268 B2
(45) Date of Patent: Mar. 30, 2010

(54) SPECTROSCOPIC UNWANTED SIGNAL FILTERS FOR DISCRIMINATION OF VULNERABLE PLAQUE AND METHOD THEREFOR

(75) Inventors: Barbara J. Marshik-Geurts, Methuen, MA (US); Huwei Tan, Cambridge, MA (US)

(73) Assignee: Infraredx, Inc., Cambridge, MA (US)

( * ) Notice: Subject to any disclaimer, the term of this patent is extended or adjusted under 35 U.S.C. 154(b) by 2005 days.

(21) Appl. No.: 10/426,750

(22) Filed: Apr. 30, 2003

(65) Prior Publication Data

US 2004/0024298 A1 Feb. 5, 2004

Related U.S. Application Data

(63) Continuation-in-part of application No. 10/212,845, filed on Aug. 5, 2002.

(51) Int. Cl.
*A61B 6/00* (2006.01)
(52) U.S. Cl. ........................................ 600/473; 600/476
(58) Field of Classification Search ................ 600/473, 600/476; 702/189; 382/128; 356/39, 51
See application file for complete search history.

(56) References Cited

U.S. PATENT DOCUMENTS

| | | | | |
|---|---|---|---|---|
| 3,463,142 A | * | 8/1969 | Harte | 600/314 |
| 4,894,013 A | * | 1/1990 | Smith et al. | 434/268 |
| 5,121,337 A | | 6/1992 | Brown | |
| 5,197,470 A | * | 3/1993 | Helfer et al. | 600/342 |
| 5,239,185 A | | 8/1993 | Ito et al. | |
| 5,441,053 A | | 8/1995 | Lodder et al. | |
| 5,596,992 A | | 1/1997 | Haaland et al. | |
| 5,678,550 A | * | 10/1997 | Bassen et al. | 600/431 |

(Continued)

FOREIGN PATENT DOCUMENTS

JP 6-505183 6/1994

(Continued)

OTHER PUBLICATIONS

Wise, B.M., et al., "Calibration Transfer by Generalized Least Squares," Seventh Scandinavian Symposium on Chemometrics (SSC7), Copenhagen, Denmark (Aug. 2001).

(Continued)

*Primary Examiner*—Eric F Winakur
*Assistant Examiner*—Katherine L Fernandez
(74) *Attorney, Agent, or Firm*—Rothwell, Figg, Ernst & Manbeck, PC

(57) ABSTRACT

Spectral variation contributed from the absorbance of unwanted correlated signals, such as blood at variable pathlengths between an in vivo catheter optic probe and a coronary vessel wall is an obstacle in the detection of vulnerable plaque. Preprocessing methods are described to reduce the impact of blood upon the spectral signal, based on the principles of Orthogonal Subspace Projection (OSP) and Generalized Least Square (GLS). The multivariate discrimination models used on the processed spectral information reduce the number of independent factors that include contributions from blood. The disclosed chemometric processing including preprocessing methods provide for in vivo spectral detection of medical analytes within the human body and in particular within the coronary vessel wall. A demonstration of how the preprocessing methods impact a discrimination modeling technique is provided, how the blood filters were developed and optimized, and finally how the OSP and GLS blood filters correct the spectral signal and improve the discrimination results of the models.

72 Claims, 10 Drawing Sheets

U.S. PATENT DOCUMENTS

| | | | |
|---|---|---|---|
| 6,016,440 | A | 1/2000 | Simon et al. |
| 6,049,727 | A * | 4/2000 | Crothall ..................... 600/310 |
| 6,095,982 | A | 8/2000 | Richards-Kortum et al. |
| 6,115,673 | A | 9/2000 | Malin et al. |
| 6,134,003 | A | 10/2000 | Tearney et al. |
| 6,321,200 | B1 | 11/2001 | Casey |
| 6,441,388 | B1 | 8/2002 | Thomas et al. |
| 6,442,408 | B1 | 8/2002 | Wenzel et al. |
| 6,475,159 | B1 | 11/2002 | Casscells et al. |
| 6,529,770 | B1 * | 3/2003 | Grimblatov ................. 600/479 |
| 6,549,861 | B1 * | 4/2003 | Mark et al. ................... 702/76 |
| 6,615,062 | B2 * | 9/2003 | Ryan et al. .................. 600/310 |
| 2001/0021803 | A1 | 9/2001 | Blank et al. |
| 2001/0047137 | A1 * | 11/2001 | Moreno et al. .............. 600/475 |
| 2003/0032064 | A1 | 2/2003 | Soller et al. |
| 2004/0142496 | A1 * | 7/2004 | Nicholson et al. ........... 436/536 |

FOREIGN PATENT DOCUMENTS

| | | |
|---|---|---|
| JP | 9-117407 A | 5/1997 |
| JP | 2000-503237 A | 3/2000 |
| JP | 2002-511294 A | 4/2002 |
| JP | 2002-214127 A | 7/2002 |
| JP | 2004-500210 A | 1/2004 |
| WO | WO 92/15008 A1 | 9/1992 |
| WO | WO 97/32182 A1 | 9/1997 |
| WO | WO 99/52434 A1 | 10/1999 |
| WO | WO 00/19889 | 4/2000 |
| WO | WO 01/074249 A1 | 10/2001 |

OTHER PUBLICATIONS

Harsanyi, J.C., "Hyperspectral Image Classification and Dimensionality Reduction: An Orthogonal Subspace Projection Approach," *IEEE Transaction Geoscience and Remote Sensing*, 32, pp. 779-785 (1994).

Ren, H., et al., "A Generalized Orthogonal Subspace Projection Approach to Unsupervised Multispectral Image Classification," *IEEE Transactionson Geoscience and Remote Sensing*, 38, pp. 2515-2528 (2000).

Martens, H., et al., "Pre-Whitening of Data by Covariance-Weighted Pre-processing," *J. of Chemometrics*, 17, pp. 1-30 (2003), in press.

Kuan, C., "Introduction to Economic Theory," *Institute of Economics, Academia Sinica* (This version: Sep. 19, 2001).

Blank, T.B., "Clinical Results from a Non-Invasive Blood Glucose Monitor," *Photonics West 2002 Meeting*, San Jose, CA (Jan. 2002).

Moreno, Pedro, R., "*Detection of Lipid Pool, Thin Fibrous Cap, and Inflammatory Cells in Human Aortic Atherosclerotic Plaques by Near-Infrared Spectroscopy*", Circulation, vol. 2002, No. 105,, Feb. 26, 2002 pp. 923-927.

Notice of Reasons for Rejection in corresponding Japanese Patent Application No. 2004-526442 (4 pages); with English translation (4 pages). (mailed by Japanese Patent Office May 25, 2009).

Cassis, L. A., et al., "Near-IR imaging of atheromas in living arterial tissue," Anal. Chem. 85:1247-1256, 1993.

Ng, L. M. And R. Simmons, "Infrared spectroscopy," Anal. Chem. 71:343R-350R, 1999.

Supplementary Partial European Search Report for EP 03 76 7194 dated Dec. 11, 2009, 4 pages.

* cited by examiner

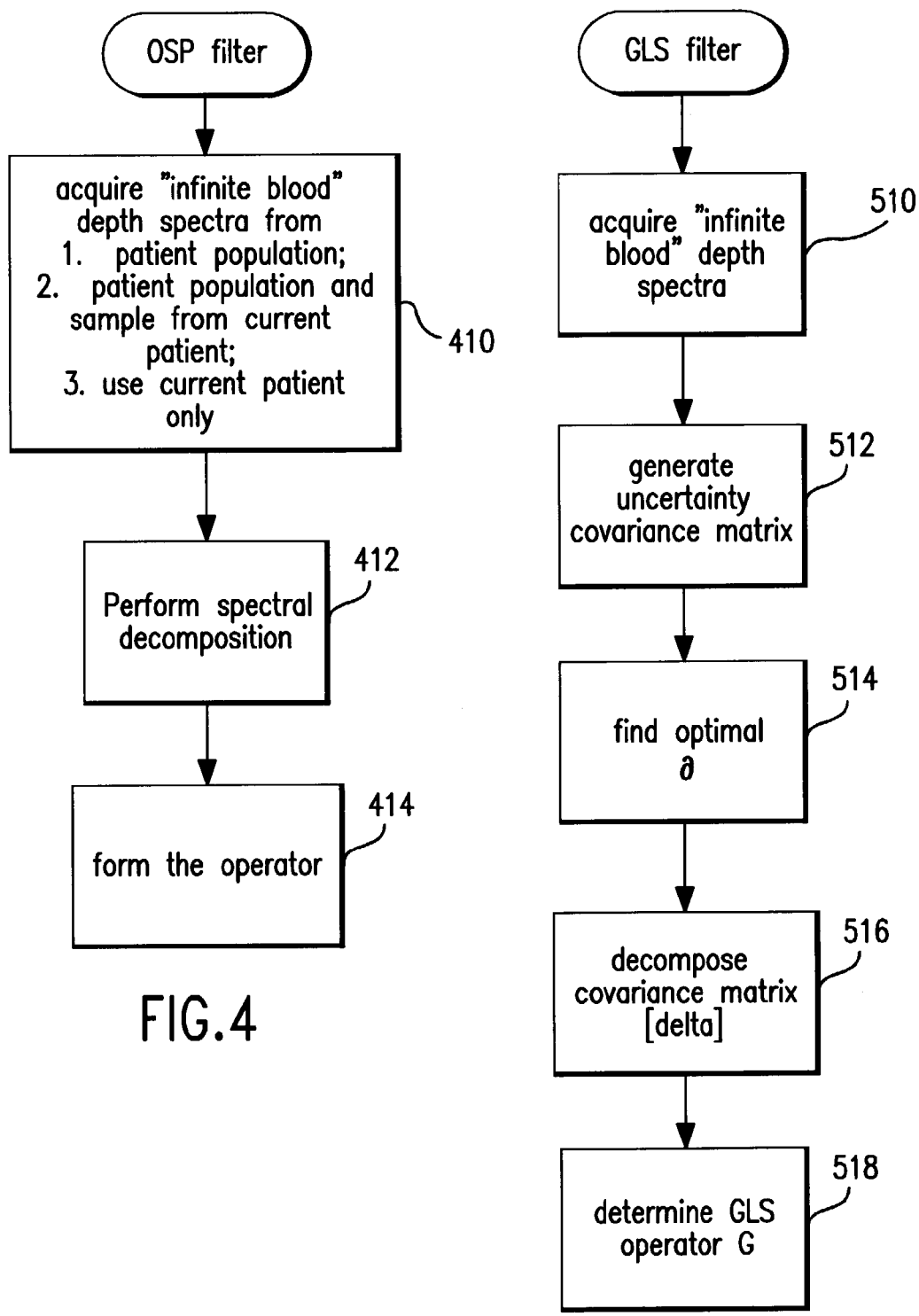

SPECTROSCOPIC UNWANTED SIGNAL FILTERS FOR DISCRIMINATION OF VULNERABLE PLAQUE AND METHOD THEREFOR

RELATED APPLICATIONS

This application is a continuation in part application of U.S. patent application Ser. No. 10/212,845, filed Aug. 5, 2002, by Barbara Marshik-Geurts, Jing Tang, and Andres Zuluaga entitled NEAR-INFRARED SPECTROSCOPIC ANALYSIS OF BLOOD VESSEL WALLS. The teachings of this application are incorporated herein in their entirety by this reference.

BACKGROUND OF THE INVENTION

Chemometrics is the science of relating measurements made on a chemical system or process to the state of the system via application of mathematical or statistical methods. It is many times used to predict the properties, such as chemical composition, of structures based on their spectral response.

The advantage of chemometric-based solutions is that they can be faster and more generally applicable than other approaches, such as direct chemical sampling. This is especially true in medical applications. One example is blood glucose monitoring, as commonly performed by diabetics. The spectroscopic transdermal chemometric assessment of blood glucose levels has been proposed as an alternative to the painful blood sampling that must be performed many times per day, in some cases.

Another application concerns the assessment of the state of blood vessel walls such as required in the diagnosis of atherosclerosis. This is an arterial disorder involving the intimae of medium- or large-sized arteries, including the aortic, carotid, coronary, and cerebral arteries. Atherosclerotic lesions or plaques can contain complex tissue matrices, including collagen, elastin, proteoglycans, and extracellular and intracellular lipids with foamy macrophages and smooth muscle cells. In addition, inflammatory cellular components (e.g., T lymphocytes, macrophages, and some basophiles) can also be found in these plaques.

Disruption or rupture of atherosclerotic plaques appears to be the major cause of heart attacks and strokes, because, after the plaques rupture, local obstructive thromboses form within the blood vessels.

Although the risk of plaque rupture usually cannot be predicted, many postmortem examinations have revealed that this risk depends mainly on plaque composition. Most ruptured atherosclerotic plaques are characterized structurally by the formation of a large, soft, lipid-rich, necrotic core covered by a thin fibrous cap, densely infiltrated by macrophages. Of these features, lipid accumulation in so-called "lipid pools" is the most frequently observed precondition for rupture. Inflammation is also a major feature of nonruptured, but eroded, thrombosed plaques.

Near infrared (NIR) spectroscopy can be used to measure and mathematical, including statistical, techniques applied to extract information from the lower resolution NIR spectral data. Mathematical manipulations such as linear regression of the spectral band of interest and classic least squares and inverse least squares and other multivariate analysis tools are available for building quantitative calibrations as well as qualitative models for discriminant analysis.

SUMMARY OF THE INVENTION

The objective is to build a system that has a catheter that is moved through the blood vessels of the patient's body to a region of interest, such as the coronary arteries, in vivo. Spectral data, such as in the NIR region, are then acquired. In one embodiment, the spectral data are from the NIR. In other examples, infrared, ultraviolet, or visible radiation spectral data sets are used. In still other examples, spectral data from fluorescence or Raman spectroscopy are used. In any case, the collected spectral data are used as a basis for chemometric analysis, to provide an assessment of the risk of heart attack, for example, in spite of the presence of spectral contributions from sources such as intervening blood, water, saline, artificial blood, and tissue components that are not related to the chemical constituents of interest.

A critical challenge here, however, concerns the limited ability to control the conditions under which the spectral data are acquired. Motion artifacts arise due to the motion pumping action of the heart. Variability in the form of the intervening blood/body fluid, pressure, pH and oxygenation levels are some examples of elements that contribute to the complexity of the analysis. Instrument-based variations can also arise, such as drift in the light source and optics over time, in addition to manufacturing variation between catheters. Moreover, the system must be very robust in order to function well in a clinical environment, where operators may have varying levels of experience.

One of the most difficult problems concerns how to address the existence of fluid, such as blood or an injected fluid that is used to displace the blood, between the catheter head, from which the signals are typically transmitted and then possibly recovered, and the vessel walls that must be analyzed. The scattering and absorbance from the intervening fluid obscures the detection of the chemical composition of the vessel walls. Moreover, the chemical composition of the blood or fluid can vary over time in a patient and the variation between patients can be substantial. Further, since the catheter head is not pinned to one spot during acquisition, especially for these in vivo applications, the path length of any optical signal through the blood is not necessarily highly controlled and can also be quite long. Nonetheless, the system must have good discriminatory ability providing diagnostic results with high sensitivity and specificity, and to accomplish this diagnostic feat a mathematical model is built.

In spite of these problems the desired signal is the spectrum of the chemical composition of the vessel wall and specifically any plaque. Characterization of the plaque is performed to determine whether it is vulnerable or not, i.e., a thin-cap fibroatheroma (TCFA) or non-TCFA. Other characterizations to determine the existence of lipid rich atheromas, fibrotic or calcified lesions, or normal tissue are possible. The unwanted or undesired signal, is the scatter and/or absorption from an intervening spectral constituent. Spectral features arising from an unwanted signal, such as that from blood, contains signatures from many variables, such as water content, temperature, pH levels, matrix bonding effects, and other chemicals, such as albumin, globulin, protein, triglycerides, and urea, which may or may not be relevant to the characterization at hand and must be removed or minimized as much as possible to permit reliable discrimination of plaques.

The present invention concerns a method and system for analyzing blood vessels in the presence of intervening blood, saline flush or other unwanted spectral signals such as artificial blood and tissue components. Specifically, the system uses preprocessing or prefiltering, to remove or diminish the contribution of the unwanted signal, such as from blood, to the spectra that are collected from the patient. After this preprocessing, the state of the blood vessel walls is assessed using quantitative or qualitative/discriminant analysis, for example. Thus, such problems as atherosclerosis can be identified and/or characterized.

In general, according to one aspect, the invention features a method for analyzing blood vessels in the presence of intervening unwanted spectral signals arising from such elements as blood, saline flush, or angiographic dye flush, for example. The process includes irradiating blood vessel walls through the blood. A spectral response is then collected, from which a spectral response of the blood vessel walls is then found by removing a contribution of the intervening unwanted spectral signals. Finally, the state of the blood vessel walls is assessed in response to the vessel's spectral response.

In specific embodiments, the step of irradiating the blood vessel walls comprises scanning a tunable source over a spectrum of interest. Collecting the spectral responses then comprises determining a time varying response of a detector during the scanning of the tunable source to resolve the spectrum. In another embodiment the irradiation step is accomplished using a broad band light source where collecting the spectral responses then comprises a time varying response in the form of a time to frequency conversion such as that performed by a Fourier Transform. In the preferred embodiment, the spectral responses are based on the light returning to a catheter head. That is, the catheter head both emits the optical signal and then collects the returning light. In other embodiments, however, a second catheter or other detector could be used to collect the response.

In the preferred embodiment, the step of determining the spectral responses of the blood vessel walls comprises applying a filter optimized to remove the spectral response or signature of the unwanted spectral component or components. In one embodiment, the "unwanted signal" spectra are collected ex vivo at a patient's bedside or at a relatively large distance from the blood vessel walls. In other embodiments, the unwanted signal spectra are derived from in vivo or ex vivo measurements to thereby maximize the degree to which the spectra are characteristic of the blood or other fluid that may intervene between the catheter head and the vessel wall.

In one embodiment, the filter is generated based on information, i.e., spectra, from prior test samples of blood or unwanted spectral signature, ex vivo or in vivo. However, in another embodiment, the filter is generated dynamically on a per patient basis, using the current patient's own blood sample or unwanted spectral signature, which is added to the prior samples to build the filter. Finally, in still other embodiments, the filter is generated dynamically using only the current patient's blood or unwanted spectral signature for the filter.

In one embodiment, the filter uses a generalized least squares analysis, based upon mathematically influencing the increase and/or decrease, of both the wanted and/or unwanted spectral signal. In another embodiment, the filter uses an orthogonal subspace projection analysis based upon mathematically decreasing the influence of the unwanted spectral signal.

In its present implementation, the step of assessing the states of the blood vessel includes performing a qualitative or discriminant analysis. In some cases the determined spectral response of the blood vessel walls is passed to an operator, who makes the final assessment. In other implementations, the assessment of the states of the blood vessel includes performing a classification analysis.

In the present implementation, the step of assessing the states of the blood vessel walls comprises determining whether the blood vessel walls are comprised of lipid pools (lipid-rich atheroma), disrupted plaques still containing some amount of pooled lipid, fibrotic lesions, calcific lesions, and/or normal tissue. Generally, the qualification, e.g., discrimination or classification, models are either based upon a two class or a single class model. In the two class model, samples can either be classified as being in the class of fibrotic, calcific, normal or other components or specimen not representative of vulnerable plaques or in the class of lipid pool, disrupted lipid pools, lipid pool/disrupted plaques or other components or specimen representing vulnerable plaques. A single class model would be classified based upon the spectrum's similarity or multivariate distance from lipid pools, disrupted lipid pools, lipid pool/disrupted plaques, or other components or specimen representing vulnerable plaques.

In one embodiment, the step of assessing the states of the blood vessel walls in response to the determined spectral responses comprises classifying the states of the blood vessel walls by means of regression analysis which may employ Partial Least Squares (PLS), PLS Discriminant Analysis (PLS-DA), Principal Component Regression (PCR), Principal Component Analysis (PCA) and other regression techniques to assess the spectral responses of the walls in the different stages of coronary artery disease. In another embodiment the assessment is made using other pattern recognition techniques using intelligent machine learning methods such as artificial neural networks, support vector machines, or fuzzy logic.

In general, according to another aspect, the invention features a system for analyzing blood vessels in the presence of intervening blood. This system comprises a source of infrared radiation, such as a tunable laser in one example, but is not restricted to this mode of radiation generation. A catheter directs the radiation to the blood vessel walls through intervening blood and collects radiation returning from the blood vessel walls. A detector system monitors the collected radiation, and a controller, such a controller for a spectrometer or photometer, resolves the spectral responses from the collected radiation detected by the detector system. Finally, an analyzer is provided for determining the spectral responses of the blood vessel walls from the collected spectral responses by removing the contribution of the unwanted signal, and then typically generating an assessment of the state of a blood vessel walls in response to the determined spectral responses.

In general, according to still another aspect, the invention features a method for de-emphasizing an unwanted spectral response in a spectral response of a structure of interest. In one embodiment, the method comprises generating a filter based on a spectral response of blood, which has been collected at a relatively large distance from the structure of interest, in this case the blood vessel walls or through a blood depth provided in a well external to the patient. A filter is then applied to the collected spectral response, which includes the blood response, to generate the spectral response of the structure of interest.

In general, it is desired to have a "spectral response" that is only based on information from the unwanted spectral signal, for example from blood or from contrast fluid. In one embodiment, this spectral response may include spectral information from other underlying tissues or structures that do not contribute to the desired signature. In another embodiment, the measured unwanted spectral signal is selected to be one that is least influenced by other structures or underlying tissue. The blood or fluid volume needed for this step depends on the design of catheter optics.

For a given catheter optical configuration, one way to determine the amount of blood needed is as follows. First, measure the spectra of blood at depth n. Then increase the depth by some amount and measure again. Iterate this process until the spectra no longer changes, which indicates that there is no influence of the underlying structures or tissue. The blood or fluid spectra could also be acquired by collecting spectra at a relatively large distance from the structure of interest or ex vivo in a specialized reference well.

According to still another aspect, the invention features a system for spectrally analyzing interior structures of animals or humans in the presence of unwanted spectral signature sources. This system comprises a source of radiation and a catheter for directing the radiation to the interior structures, which can then be directed through an intervening medium or no medium, then collecting the radiation returning from the interior structures. A detector system is provided for monitoring the radiation from the interior structures. A spectrometer controller generates the spectral responses from the radiation detected by the detector system. An analyzer determines spectral responses of the interior structures from the generated spectral responses from the spectrometer controller by removing a contribution of the medium, and then generates an assessment of the state of the internal structures, in response to the determined spectral responses of the internal structures.

In general, according to another aspect, the invention features a method for reducing the unwanted spectral signal in the analysis of blood vessels. The method comprises collecting spectral responses of the blood vessels along with the unwanted spectral responses. The unwanted spectral contributions could be from sources such as intervening blood, water, saline, contrast dye, artificial blood, and tissue components that are not related to the chemical constituents of interest. The collected spectral responses are then processed to reduce the unwanted spectral signatures relative to the blood vessel responses to generate determined spectral responses of the blood vessels, which are used to analyze the blood vessels.

In the current invention, the method of generating the spectral responses uses NIR spectroscopy. The spectral responses are mathematically processed to remove offsets and/or slopes, remove spectral scatter, or enhance the signal to improve prediction accuracy. These processing methods accomplished using algorithms processed by a computer processor or embedded upon a chip, but the invention is not restricted to these methods.

Processing the spectral responses can comprise enhancing or up-weighting the blood vessel spectral responses and/or de-emphasizing or down-weighting the unwanted spectral signature. The unwanted spectral signal can be based on temperature fluctuation, heart motion, variation from the inconsistent pathlength due to different intervening fluids or space between the catheter probe and the blood vessel wall due to catheter motion, in addition to spectral contributions from sources such as intervening blood, water, saline, artificial blood, and tissue components that are not related to the chemical constituents of interest.

In the section below it will be demonstrated that advanced chemometrics techniques for scatter removal algorithms, such as standard normal variate (SNV) and multiple scatter correction (MSC), and signal filtering processes such as orthogonal subspace projections (OSP) and generalized least squares (GLS) can significantly improve the spectral response of the lipid pool signal through an unwanted spectral signal such as blood. The OSP and GLS blood filters are able to extract the statistical characteristics of the variability of the unwanted signals and render them inconsequential to the model.

By combining several preprocessing/pretreatment methods with the unwanted spectral signal filter, the models significantly outperformed all other preprocessing methods. These methods will allow in vivo models to be built that disregard differences between each patient due to unwanted spectral signatures from for example blood variability and will allow for more robust models to be built.

The above and other features of the invention including various novel details of construction and combinations of parts, and other advantages, will now be more particularly described with reference to the accompanying drawings and pointed out in the claims. While this invention will be particularly shown for NIR spectroscopy and analysis methods will be described with references to preferred embodiments thereof, it will be understood that the particular method and device embodying the invention are shown by way of illustration and not as a limitation of the invention. The principles and features of this invention may be employed in various and numerous embodiments without departing from the scope of the invention. The unwanted spectral signal filter may be used in particular with blood or in general with any undesired spectral signal that impedes the assessment of the blood vessel walls.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 4 is a flow diagram illustrating a method for generating an OSP filter for spectral preprocessing to enhance a spectral response of the blood vessel walls, according to the present invention;

FIG. 5 is a flow diagram illustrating a method for generating a GLS filter for spectral preprocessing to enhance a spectral response of the blood vessel walls, according to the present invention;

Figure 9:
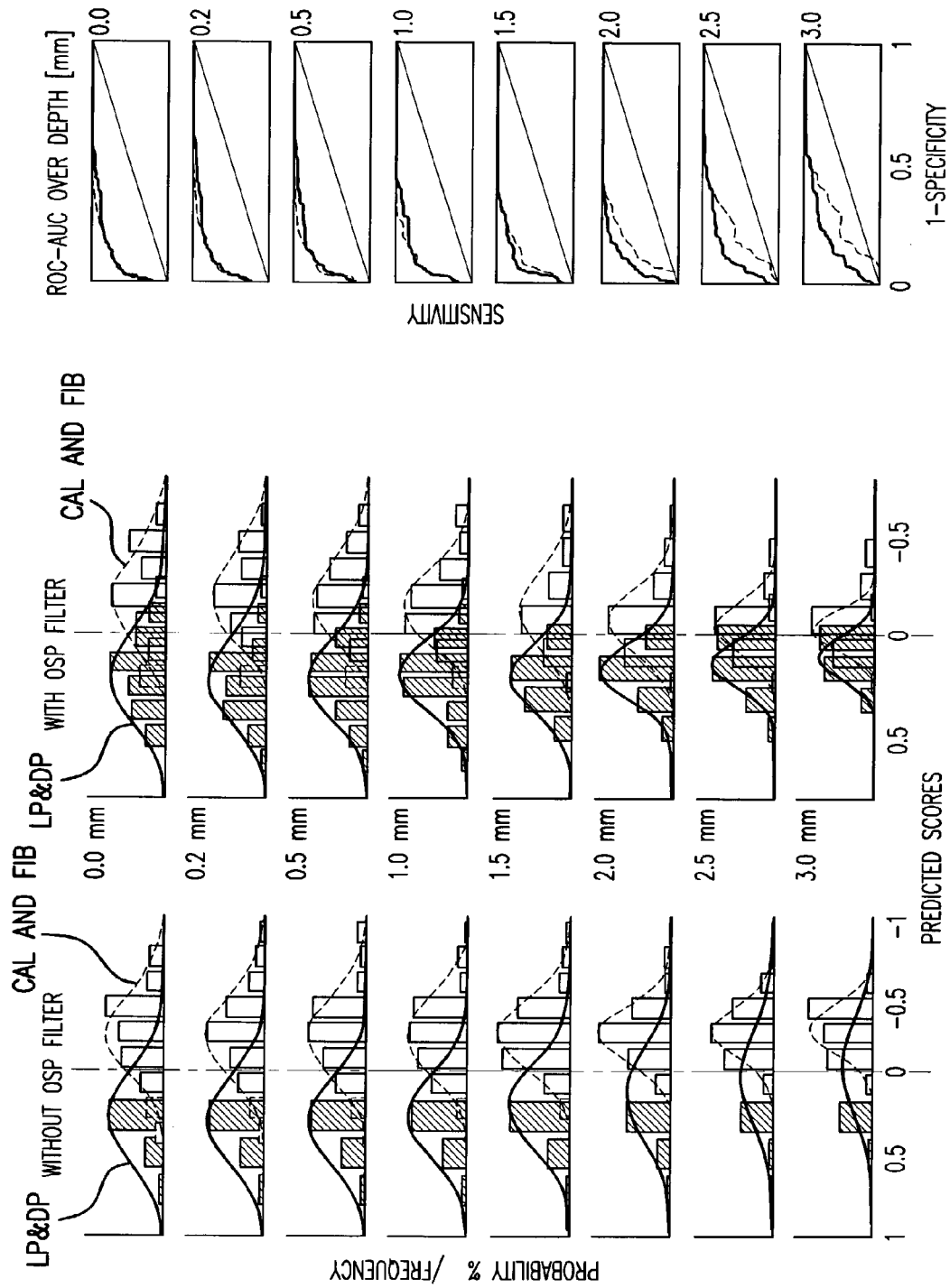
Figure 10:
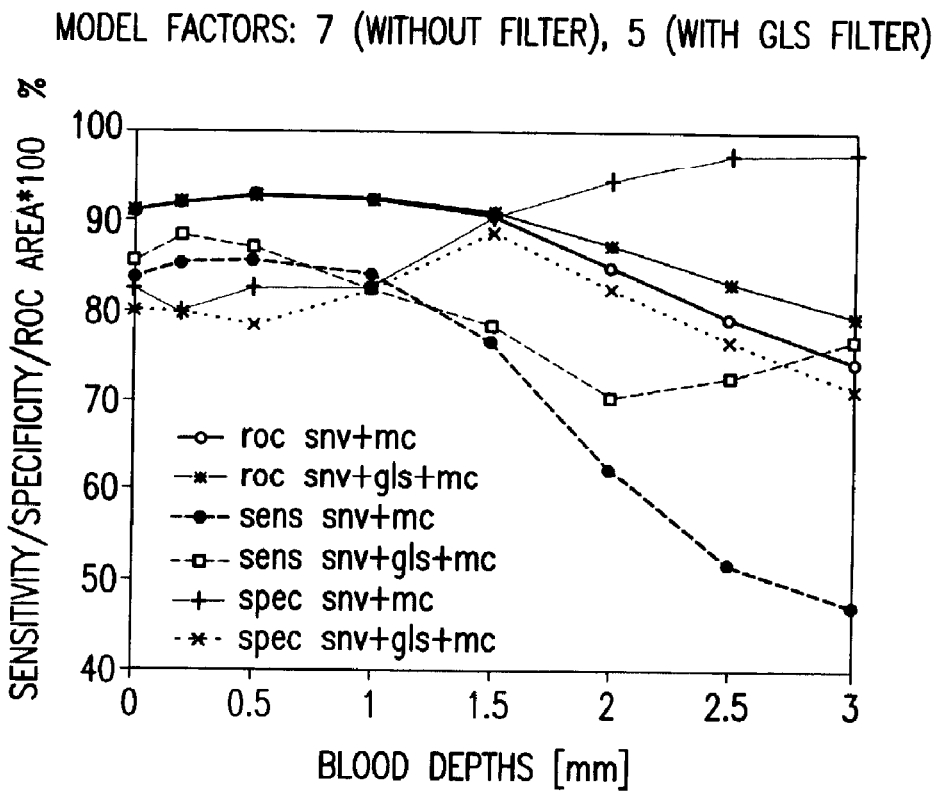
Figure 13:
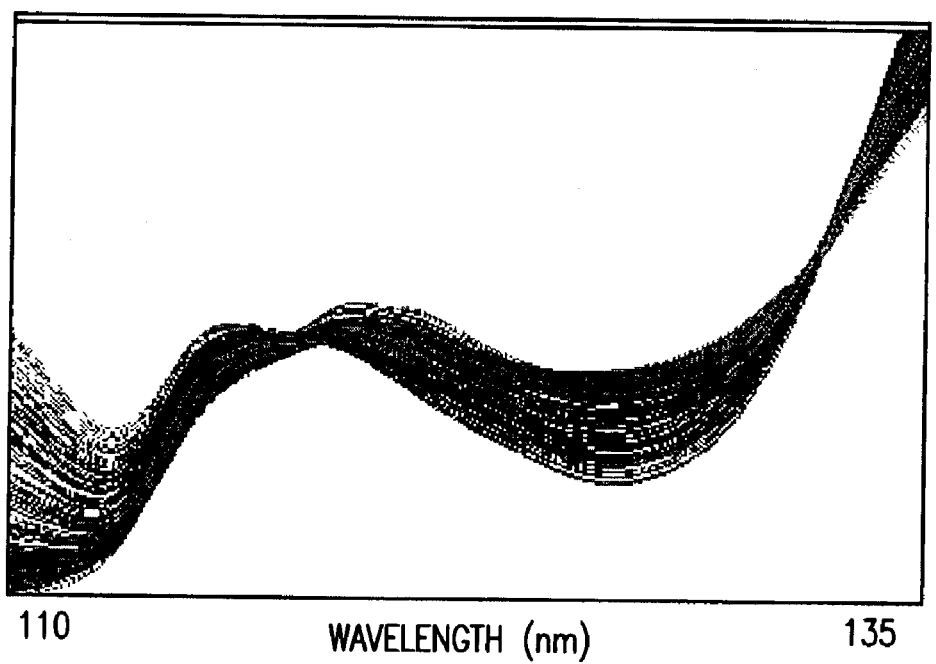
Figure 11:
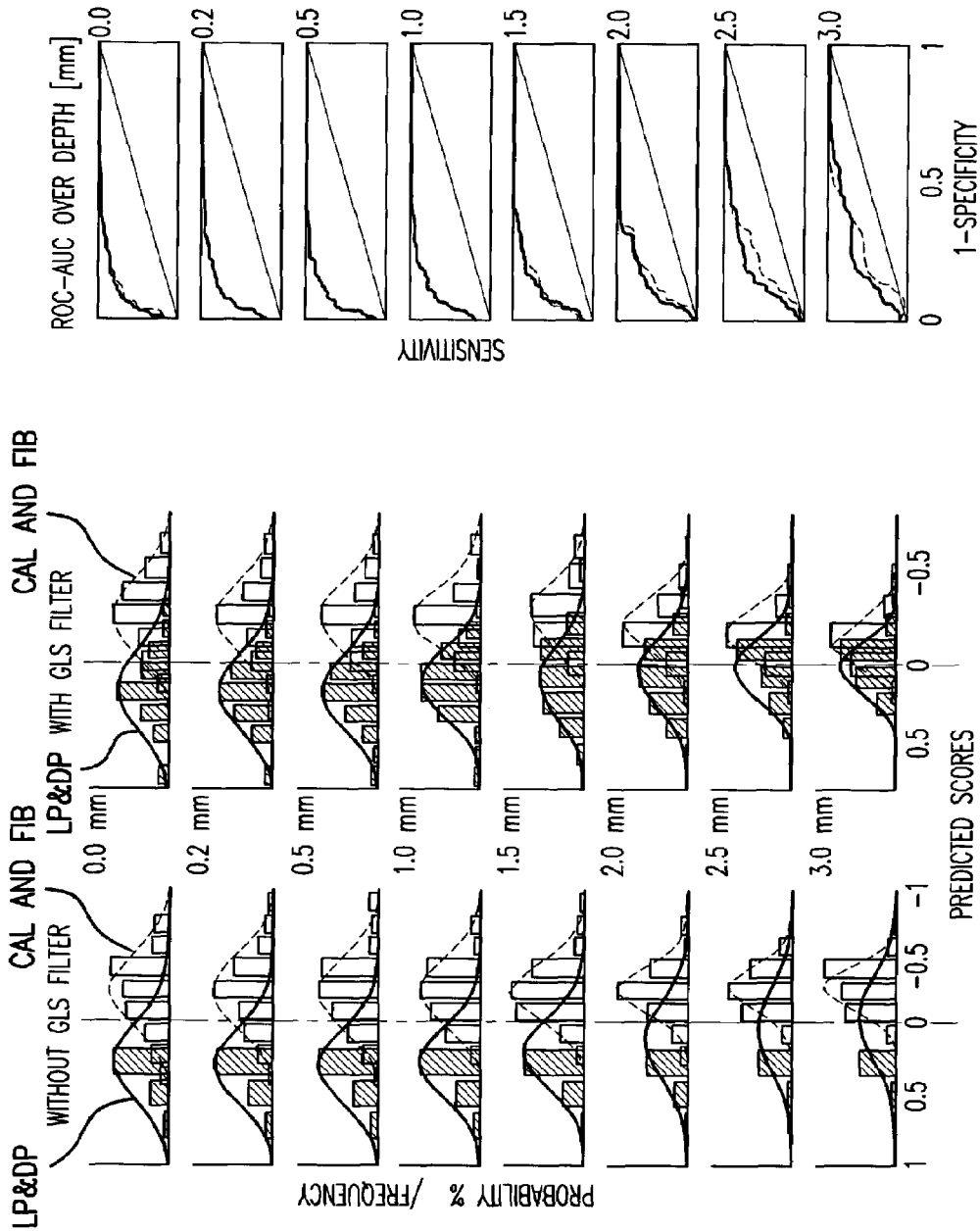
Figure 12:
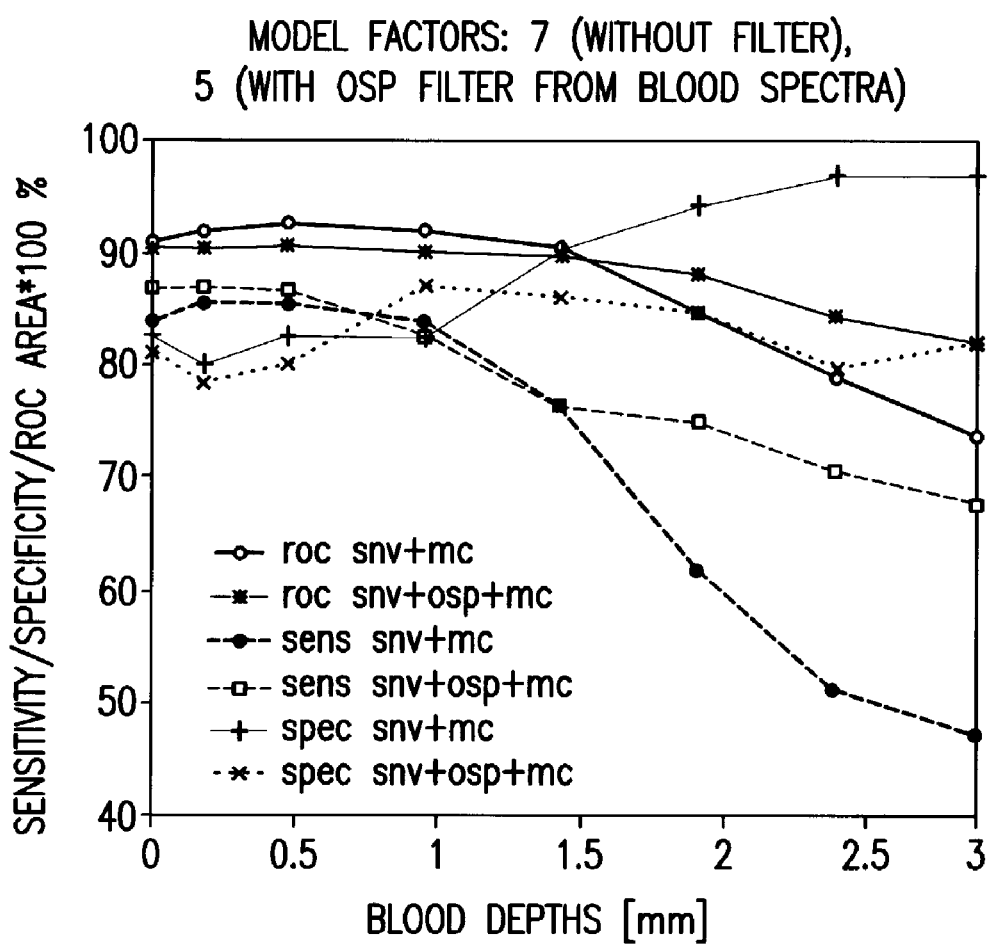

sensitivity (SENS), specificity (SPEC), or the percentage of the receiver operating characteristics area under the curve (ROC-AUC) (×100);

FIG. 9 shows graphs of the prediction scores (x-axis) and distributions (y-axis) for the blood depths from 0.0 to 3.0 for PLS-DA models with Standard Normal Variance and Mean Centering (SNV+MC) (column one) or Standard Normal Variance, Orthogonal Subspace Projection and Mean Centering (SNV+OSP+MC) (column two) preprocessing; the histogram on the left side is the distribution of the Lipid Pool (LP) and Disrupted Plaque (DP) sample prediction results and the right hand side histogram is the distribution of the Fibrotic (FIB) and Calcific (CAL) sample prediction results; the central black line is the model threshold; column three is a plot of the ROC-AUC as a function of blood depths with the x-axis (1-Specificity) and the y-axis Sensitivity;

FIG. 10 is a plot in which the X-axis is the Blood Depths in mm and the Y-axis is one of the following: SENS, SPEC or ROC-AUC (×100) percentage. The results are shown for no filter (using SNV and MC only) or with the generalized least squares (GLS) filter;

FIG. 11 shows graphs of the prediction scores (x-axis) and distributions (y-axis) for the blood depths from 0.0 to 3.0 for PLS-DA models with SNV+MC (column one) or SNV+GLS+MC (column two) preprocessing, the left hand side histogram is the distribution of the LP and DP samples and the right hand side histogram is the distribution of the FIB and CAL samples, the central black line is the model threshold; column three is a plot of the ROC-AUC as a function of blood depths with the x-axis (1-Specificity) and the y-axis Sensitivity;

FIG. 12 is a plot in which the X-axis is the probe-to-specimen depths with blood intervening in mm and the Y-axis is one of the following: SENS, SPEC or ROC-AUC (×100) percentage, the results being shown for no filter (using SNV and MC only) or with the orthogonal subspace projection (OSP) filter; and FIG. 13 is a plot showing the spectral responses of LP and DP samples preprocessed using SNV only, the y-axis is arbitrary absorbance units and the x-axis is wavelength in nanometers (nm).

DETAILED DESCRIPTION OF THE PREFERRED EMBODIMENTS

The present invention addresses the generation of spectral data in vivo and the mathematical manipulation or filtering of that data in order to extract or determine a portion of the spectrum that results from structures of interest, which here are the blood vessels walls. Finally, the state of vessel walls is assessed based on this extracted or determined spectrum, such that the system either generates a conclusion as to the state of the vessels or the extracted or determined spectral response from the data is supplied to the operator, who generates the conclusion.

A number of techniques or technologies are currently contemplated for generating the spectral data. Generally, spectroscopy is the science of the measurement of electromagnetic radiation as it is absorbed or emitted by molecules or their atoms as they move from one energy level to another. When a molecule is subjected to radiation, the atoms can absorb a portion of the radiation at frequencies corresponding to resonances of structures within the atoms or molecules. Many portions of the electromagnetic spectrum can be used for this task, including gamma-rays, x-rays, ultraviolet, infrared, microwaves, to audio/radio frequency radiation. Specific techniques that could benefit from this method include absorption spectroscopy, Raman spectroscopy, and fluorescence spectroscopy, for example. In the specific method involving infrared radiation (of which NIR is a subset) the key component to the infrared transition, is that the molecule must have a non-zero dipole moment in order for the transition to occur, therefore linear diatomic molecules such as $N_2$ and $H_2$ are not active in the infrared region while HCl and the functional group C=0 have very strong signals. Many of the chemical components involved in the make up of the vessel walls are composed of molecules that have a dipole moment making them eligible for excitation and detection in the NIR region.

The in vivo environment in which the spectral data are collected is, however, dominated by unwanted spectral signature from many sources and poorly controlled. The collected spectra are therefore preprocessed and/or filtered in order to highlight the response of the vessel walls. Typically, the largest unwanted spectral signal source is the blood, or other fluid that is used to flush the blood, from the path between the catheter head and the structures of interest. A general challenge faced by in vivo applications concerns an inability to control the physical relationship between the catheter head and the structures of interest, thus making it difficult to predict the amount of unwanted spectral signals that will be present at any one time.

In an effort to obtain the true or accurate assessment of the state of the vessel walls, the spectral response is subjected to the improvement or enhancement of the desired spectral signal through the suppression of the unwanted signal, according to the invention. This assessment can include a qualitative classification or discrimination process. A quantitative analysis assessment can also be used. Further, the determined spectral response can be provided to an operator, who makes the ultimate assessment.

Qualitative or pattern recognition algorithms use computerized mathematical models developed by modeling the relationship between spectra and tissue states of known tissue samples. These models are typically based on large amounts of patient data or ex vivo data simulating in vivo data and chemometric techniques such as Partial Least Squares Discrimination Analysis (PLS-DA), Principal Component Analysis with Mahalanobis Distance and augmented Residuals (PCA/MDR), and others such as PCA with K-nearest neighbor, PCA with Euclidean Distance, soft independent modeling by class analogy (SIMCA), the bootstrap error-adjusted single-sample technique (BEST), or can be analyzed using machine learning methods such as neural networks, fuzzy logic, or support vector machines and other types of pattern recognition tools.

Spectral Data Generation

The invention has applicability to a variety of techniques for acquiring the spectral data. In the current embodiment, discussed in detail below, the spectral data are generated optically. Currently, the near infrared spectral region of the infrared radiation spectrum is used.

Optically Generated Spectral Data

Figure 1:
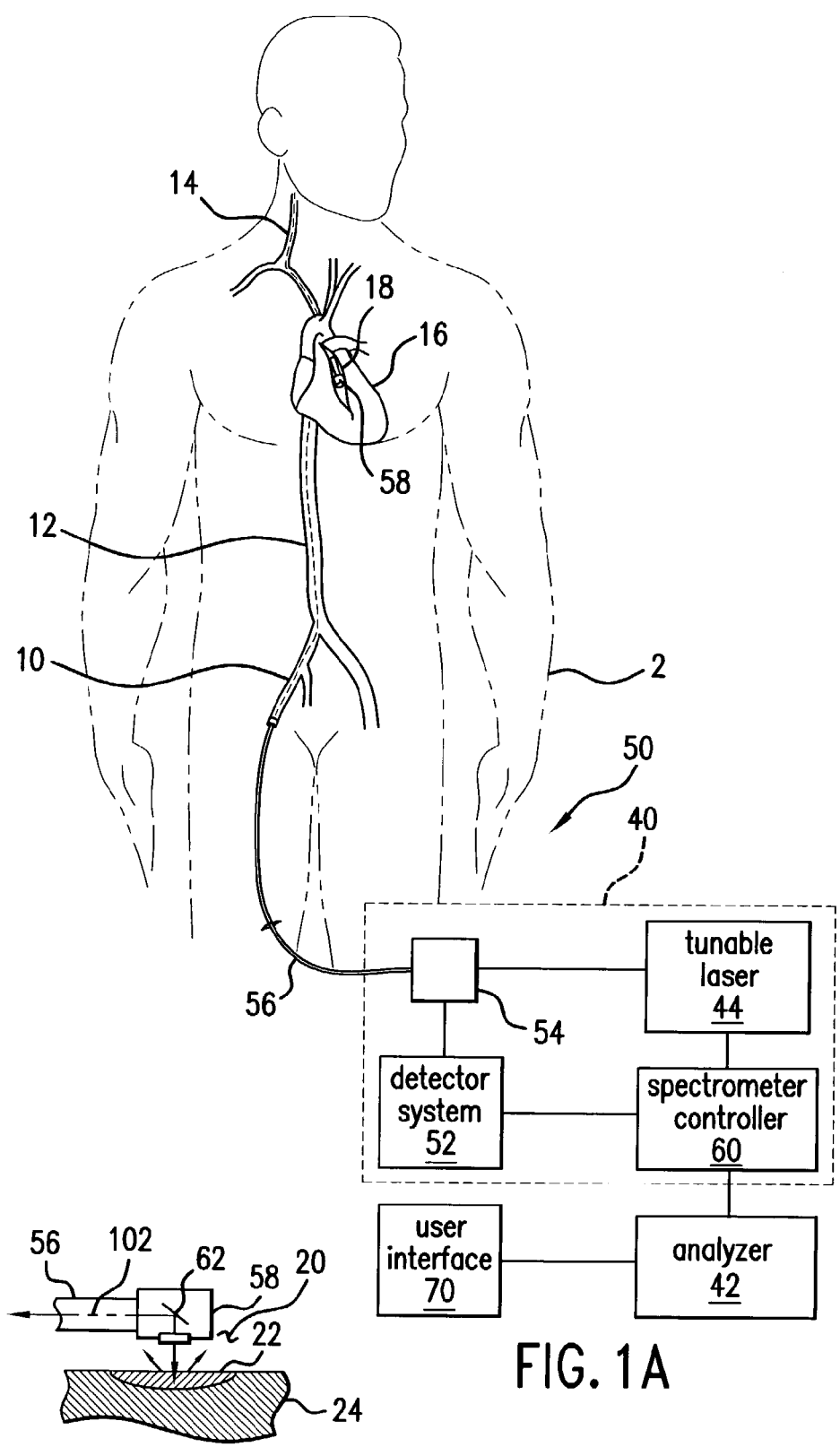
FIG. 1A is a schematic block diagram illustrating the spectroscopic catheter system to which the present invention is applicable.
FIG. 1B is a cross-sectional view of the catheter head positioned for performing spectroscopic analysis on a target region of a blood vessel.

FIG. 1A shows an optical spectroscopic catheter system 50 for spectroscopic analysis, to which the present invention is applicable, in one embodiment. It generally comprises a catheter 56, a spectrometer 40, and analyzer 42.

In more detail, the catheter 56 includes an optical fiber or optical fiber bundle. The catheter 56 is typically inserted into the patient 2 via a peripheral vessel, such as the femoral artery 10. The catheter head 58 is then moved to a desired target area, such as a coronary artery 18 of the heart 16 or the carotid artery 14. In the embodiment, this is achieved by moving the catheter head 58 up through the aorta 12.

When at the desired site, radiation is generated. In the current embodiment optical radiation is generated, preferably by a tunable laser source 44 and tuned over a range covering one or more spectral bands of interest using for example, a tunable filter or grating. It is coupled into the optical fiber of the catheter 56 to be transmitted to the catheter head 58. In another embodiment, a broad band light source can be used covering one or more spectral bands using for one example, a tunable filter or grating. In another embodiment the broad band light source is sent in as a packet of all wavelengths with wavelengths selected using, for example, an interferometer.

In the current embodiment, optical radiation in the near infrared (NIR) spectral regions is used for absorption spectroscopy. Exemplary scan bands include 1000 to 1450 nanometers (nm) generally, or 1100 nm to 1350 nm, 1150 nm to 1250 nm, 1175 nm to 1280 nm, and 1190 nm to 1250 nm, more specifically. In other embodiments the NIR spectral scan regions include bands from the 1000 to 1450 nm along with bands in the region from 1600 to 1800 nm. In other embodiments, the NIR spectral scan region extends from 900 to 2500 nm, in some cases using only those regions optimized by the data used to build the models.

However, in other optical implementations, scan bands appropriate for fluorescence and/or Raman spectroscopy are used. In still other implementations, scan bands in the visible or ultraviolet regions are selected.

With reference to FIG. 1B, the optical signal 102 from the optical fiber of the catheter 56 is directed by a fold mirror 62, for example, to exit from the catheter head 58 and impinge on the target area 22 of the artery wall 24. The catheter head 58 then collects the light 102 that has been partially absorbed, reflected, refracted and/or diffracted (scattered) from the target area 22.

Returning to FIG. 1A, the returning light 102 is transmitted back down the optical fibers of the catheter 56 to a splitter or circulator 54 or in separate optical fibers. This provides the returning radiation to a detector system 52, which can comprise one or multiple detectors.

A spectrometer controller 60 monitors the response of the detector system 52, while controlling the source or tunable laser 44 in order to probe the spectral response of the target area 22 through the intervening blood or other unwanted signal source 20.

As a result, the spectrometer controller 60 is able to collect spectra by comparing the time varying response of the detector system 52 to the instantaneous wavelength of the tunable laser 44. When the acquisition of the spectrum is complete, the data are then provided by the spectrometer controller 60 to the analyzer 42.

In other embodiments, a combination of a broadband source and a spectrometer are used to collect the spectra instead of the tunable laser and detector. The specific configuration is not critical to the invention. For example, Fourier analysis can also be used to resolve the wavelength dependent responses of the spectra collected using a broadband light source and an interferometer.

In other embodiments, the spectrometer is replaced with a photometer to acquire the spectral information. Rather than generate continuous spectral information, like spectrometers (spectrophotometers), a photometer typically comprises a series of wavelength filters mounted on a turret wheel and a single detector. They also typically have several monochromatic light sources, such as light-emitting diodes.

In still other embodiments, the light or radiation is not necessarily emitted and collected through the same catheter head. Instead, the radiation is emitted from one location such as a first catheter, which is inside or outside the vessel, and then received at another location, such as second catheter head, which is also either outside or inside the vessel, respectively. The second catheter head collects the light and transmits it to the detector system of the spectrometer. Typically one catheter is inside the vessel and the other catheter is outside the vessel.

However the spectra are collected, the analyzer 42 makes an assessment of the state of the blood vessel wall 24 and, specifically area 22 that is opposite the catheter head 58, from collected spectra, in the present embodiment. The collected spectral response is used to determine whether the region of interest 22 of the blood vessel wall 24 comprises a lipid pool or lipid-rich atheroma, a disrupted plaque, a vulnerable plaque or thin-cap fibroatheroma (TCFA), a fibrotic lesion, a calcific lesion, and/or normal tissue. This information is provided to an operator via a user interface 70, or the raw discrimination or prediction analysis results from the corrected spectrum is provided to the operator, who then makes the conclusion as to the status of the region of interest 22.

In one embodiment the information provided by the analyzer 42 discriminates one classification group from all other spectra features. In another embodiment, the analyzer 42 provides classification between two or more classes from each other. In still another embodiment, prediction results provide a scale for ranking the response with respect to one of the classifications groups, such as a lipid pool. In a still further embodiment, the information provided is used to quantify the presence of one or more chemical constituents that comprise the spectral signatures of a normal or diseased blood vessel wall.

Figure 2:
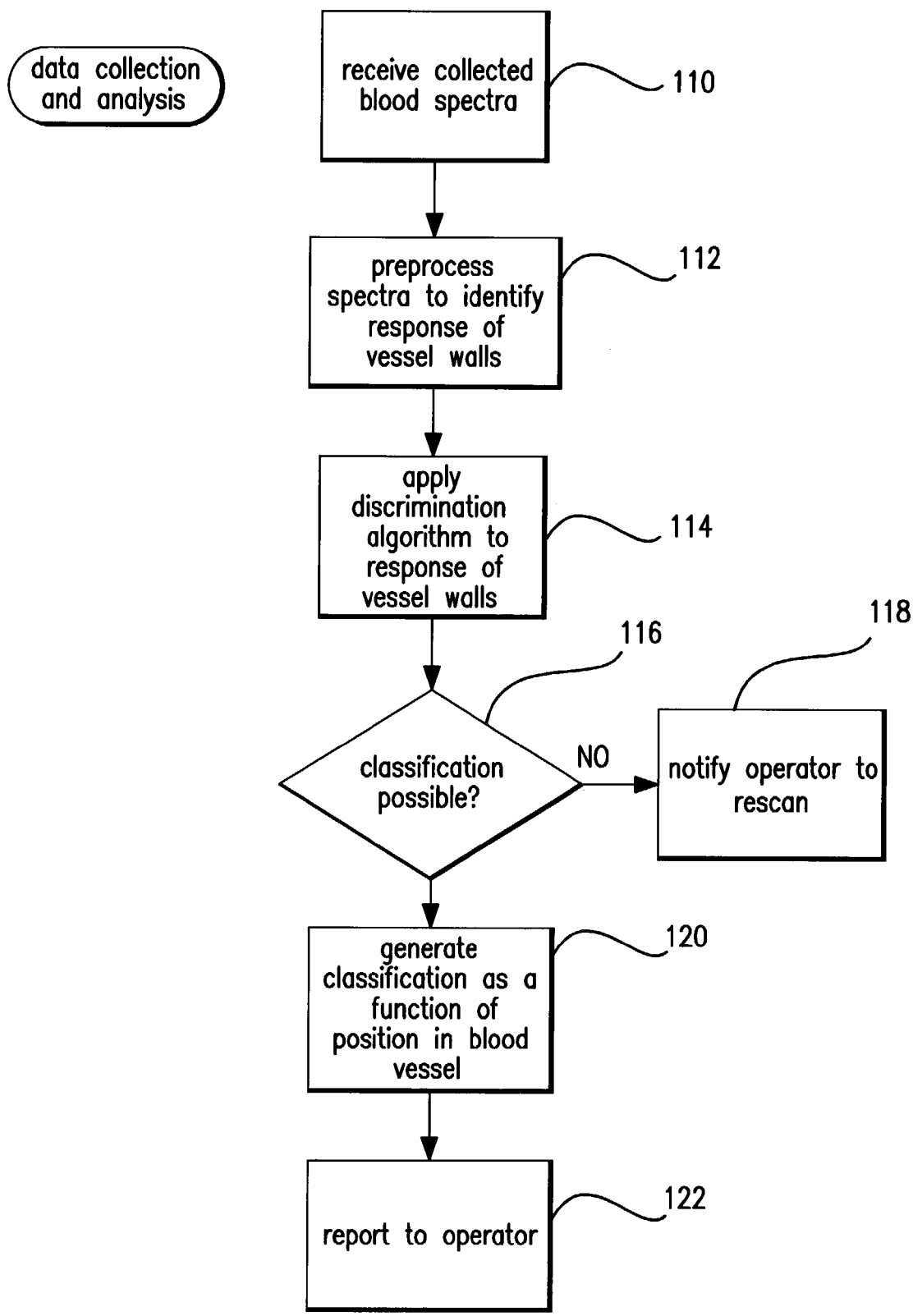
FIG. 2 is a flow diagram illustrating a method for analyzing blood vessels in the presence of intervening blood, other fluid, or unwanted spectral signal according to the present invention.

FIG. 2 illustrates a method for analyzing blood vessels in the presence of intervening blood, other fluid, or other unwanted spectral signals, which is performed by the analyzer 42. Specifically, in step 110, the analyzer 42 receives the collected spectra from the spectrometer controller 60. These collected spectra are a composite response typically of both the region of interest 22 of the blood vessel wall 24 and the intervening fluid 20, such as blood, that is along the optical path between the catheter head 58 and the region of interest 22. Sometimes the intervening fluid 20 is another fluid that was used to remove the blood from the path, such as water, saline, contrast dye, artificial blood, or a gas contained in balloon catheter, for example.

In step 112, the analyzer 42 preprocesses these collected spectra to identify the response of the vessel walls. The preprocessing of the collected spectra emphasizes the response of the vessel walls relative to the response of the unwanted spectral signal, such as the spectral response and scattering of the intervening blood, other fluid, or other unwanted spectral signatures 20.

In the preferred embodiment, the preprocessing removes, filters-out, or deemphasizes the contribution to the intervening unwanted spectral signatures, thereby leaving the response of the vessel walls.

However, in alternative embodiments, the response of the vessel walls is emphasized relative to the response of the unwanted spectral signatures.

In step 114, the analyzer 42 applies a discrimination algorithm to these determined responses of the vessel walls. The discrimination algorithm creates a model corresponding to the various states of interest of the blood vessel walls. These include states that are classified as calcific lesion, fibrotic lesion, normal tissue, disrupted plaque, thin-cap fibroatheroma (TCFA), lipid pool, lipid-rich atheroma or other descriptors for the state of coronary artery disease and in particular the state currently described as high risk vulnerable plaques. Other states such as proteoglycan-rich tissue are also possible in other implementations. Based on where the strongest correlation arises, the analyzer 142 is able to make a prediction as to the state of the region of interest 22 of the blood vessel wall 24. Alternatively, the analyzer enables the operator or physician to perform the analysis by providing the discrimination prediction values without applying the threshold that separates the classes into different groups. In another embodiment the discrimination means is a pattern recognition algorithm that can separate most or all of the states into separate classes.

In step 116, in one embodiment, the analyzer 42 looks at the result produced by the discrimination algorithm and makes an assessment as to whether or not classification is possible. That is, it looks at the strength of the correlation and determines if a prediction or a diagnosis can be made, which provides acceptable levels of error, such as false positives and false negatives. If classification is determined to not be possible, the analyzer 42 notifies the operator through the user interface 70 to rescan the area of interest 22 in step 118. In another embodiment, the discrimination algorithm predicts the unknown samples and supplies a value that is mapped to a gray-scale or color-scale that is correlated to the discrimination ability of the model, from which the operator then determines a course of action.

In contrast, if the discrimination algorithm produces an above threshold result that is strongly correlated to one of the states of interest, the analyzer 42 produces a classification for the region of interest 22 of the blood vessel 24 in step 120. Finally, in step 122, a report is provided to the operator through the user interface 70 that sets forth the state of the vessel walls as a function of position, thereby showing regions of normal tissue and regions containing calcific lesions, fibrotic lesions, disrupted plaques, or lipid pools, according to one classification scheme. Another embodiment will show the gray- or color- scales, which are correlated to the information of the disease state of the blood vessel wall. Large positive values indicating more high-risk vulnerable plaque disease or thin-cap fibroatheroma (TCFA) and more negative values indicating other disease states that are not high risk vulnerable plaques.

In other embodiments, the analyzer 42 assessment is a quantitative result that is provided to the operator. Such a result includes, in one embodiment, the distribution of various chemical components of interest in the blood vessels. In another embodiment the various chemical components of interest are presented as quantities such as concentration values. This information is provided to the operator, who then makes the conclusions concerning the state of the blood vessel walls.

Figure 3:
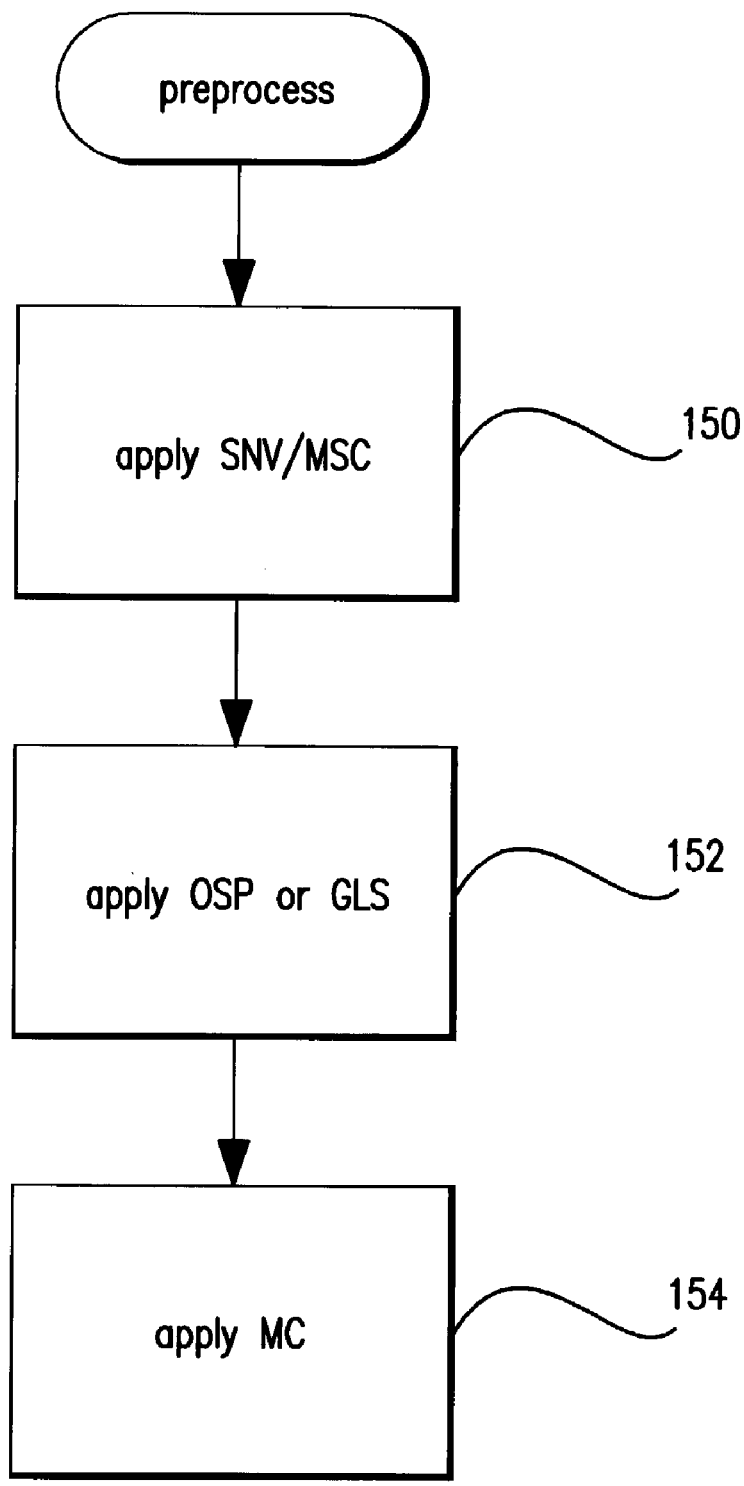
FIG. 3 is a flow diagram illustrating spectral preprocessing for enhancing a spectral response of the blood vessel walls according to one embodiment of the present invention.

FIG. 3 shows the steps performed in the preprocessing 112 of FIG. 2, in one embodiment. This involves the removal or de-emphasis of the response or spectrum of the intervening blood or other interferant 20 along the optical path.

The preprocessing method focuses on removing interferants unrelated to the signal of interest, such as the baseline slope, the offset, and/or the linear or multiplicative effects of scattering related to the instrument, the environment, or other interferants including blood, saline, or dye, for example. Some examples of methods used to remove these effects are standard normal variance (SNV) or multiplicative signal or scatter correction (MSC) analysis 150 together or without further mean centering (MC) 154. To enhance the small spectral features pertaining to the component of interest the data can be processed using a variety or methods currently know, such as MC, autoscaling, normalizing, smoothing using Savitsky Golay smoothing, detrending, wavelet filtering, finite impulse response (FIR) filtering, along with other methods and combinations thereof. Other processing such as first and second derivative filtering, varied baseline removal techniques, and orthogonal signal correction are used in some implementations. The application of these pre-processing methods prior to the application of the unwanted spectra signal filter further increases the prediction power of the model by removing the multiplicity effect and to remove the baseline, slope and offset.

According to the invention, generalized least squares analysis (GLS) or orthogonal subspace projection analysis (OSP) is performed as an intervening step 152. Generally, this "unwanted signal filter" step corrects for the impact of an unwanted spectral signature upon the NIR spectrum, enhancing the signal of interest relative to the unwanted signal.

Unwanted Spectral Signal Filter Algorithms

The basic linear algebra regarding the algorithms used for the unwanted spectral signal filters can be formulated as follows in Equation (1). Consider the equation:

$$X=R+Z+E \quad (1)$$

X represents the matrix of spectra that will be used to build the calibration model. These spectra can be decomposed into three separate component matrices: the desired signal matrix R, the undesired variation matrix Z, and the white noise matrix E. The goal of the unwanted signal filter algorithm is to eliminate the largest variation within Z prior to building the calibration model. Because Z can be separated from R mathematically and statistically this goal is achievable.

In the specific case of the removal of the blood spectrum, there are a number of independent factors driving the spectral influence. Spectral features associated with the chemical components of vulnerable plaque are of most interest and are to be retained in R in Equation (1), while factors such as those associated with blood variation, blood depths, temperature fluctuation, heart/catheter motion, and/or other tissue properties, which are deemed undesirable, can be grouped into the spectral term Z. In some cases however, R may only represent 1% or less of the spectral variation with the majority represented by Z. By the application of a specific mathematical operator O, the spectral influence of Z can be minimized or even removed from the spectral signals in X, resulting in the corrected spectral matrix $X_{corrected}$ shown in Equation (2).

$$X_{corrected}=OR+OE \quad (2)$$

The newly corrected spectral signals, $X_{corrected}$, are now only a function of the underlying tissue signal R and the white noise E, unencumbered by the absorbencies attributed to blood or Z.

After preprocessing the spectral data, which reduces the dimensionality of the signals, the spectral features of interest have been enhanced. Simple and robust models are subsequently achieved with an improved prediction power. And the prediction results are easier to interpret.

OSP Algorithm

Orthogonal subspace projection (OSP) was developed to correct background energy of image pixels for hyperspectral image classification in 1994. The original idea of OSP was to annihilate all unwanted or undesired spectral signatures (background) within a pixel, which is similar to orthogonal signal correction (OSC) that was extensively investigated in recent years by chemometricians.

In the case of the OSP algorithm, the operator O required to remove the interfering signal (or the undesirable matrix Z) can be estimated by the decomposition of the spectra into a few principal components (factors) that are associated with the unwanted signal such as blood, described above. Equation (3) represents the estimated undesired signal $\hat{Z}$:

$$\hat{Z} = TP^T \quad (3)$$

where P is a set of basis vectors that are dependent upon, or derived from the spectra of, the undesirable signal, $P^T$ is the mathematical transpose of the matrix P, and T is the scores matrix from the subspace that is spanned by the bases vectors P.

If P can be estimated or is known using a priori knowledge, the operator O can be developed to eliminate the effects of Z, the undesired signatures from the original spectra in X. To accomplish this, an operator is found that projects T onto a subspace that is orthogonal to the columns of P. This operator is:

$$O = I - P P^+ \quad (4)$$

where I is the identity matrix, P is the estimated unwanted spectral signal that is to be removed and more specifically represents the basis vectors that represent the spectral feature or signature to be removed, and $P^+$ is the pseudo inverse of P or $(P^T P)^{-1} P^T$. Applying this operator or unwanted signal filter, O, to Equation (5), it reduces to:

$$X_{OSP} = OR + OE \quad (5)$$

This filter is an optimal interferences rejection operator in the least squares sense, since O annihilates the spectral contribution of Z to zeros.

The question is how to find the basis vectors, P, by using a priori knowledge. OSC is one way to do this. OSC employs the signal matrix X and target analyte Y and uses an algorithm to iteratively exclude the undesired signature from X according to the information in Y until a final convergence for P is obtained. However, if the target Y block is merely a binary representation of the two groups (a 1 or a 0), this proves to be a weak indicator for the undesired spectral characteristics. Therefore when applying this method to classification or discrimination type data, OSC is not a good estimator of P.

FIG. 4 illustrates one method for the application of an OSP-based filter to spectral data. It only requires the spectral information in order to create the operator O. The spectra used in this case are those of the unwanted spectral signatures and in particular for this case it is the spectra collected from "infinite" blood or fluid depths, which have been determined to consist of the undesired variation. These spectra are collected at very long pathlengths in vivo or in vitro by the analysis of a collected blood or fluid sample and/or using multiple samples in step 410 during the model build up.

In one embodiment, the model is generated based on information, i.e., spectra, from prior test samples of blood or unwanted spectral features, ex vivo and/or in vivo. These samples are collected from large populations of individuals who exhibit the range of different blood chemistries. The system, in one embodiment, further adapts the model over time to improve its performance as further spectra are collected during the operation and to optimize the model for the unique performance characteristics of the device. However, in another implementation, the filter is generated dynamically on a per patient basis, using the current patient's own blood sample or unwanted spectral signature, which is added to the prior samples to build the filter. This is a robust approach since it allows for optimization on a per-patient basis yet accounts for the new information acquired on the unwanted spectral signatures over time. Finally, in still another implementation, the filter is generated dynamically using only the current patient's blood or unwanted spectral signature for the filter.

The spectra of the unwanted spectral signature are collected either in vivo or ex vivo. For example, in one embodiment the unwanted spectral signature of blood samples are placed in a long well to simulate a long or effectively infinite path length. This can performed as part of an initial calibration operation or in the clinical setting with a sample of the current patient's blood. In another embodiment, the spectra are collected in vivo by monitoring when there is a large distance, such as greater than a few millimeters and preferably more than 5 millimeters, between the catheter head and the blood vessel wall. Preferably, blood vessels exhibiting normal tissue (NML), or known characteristics are used. The existence of this physical relationship is determined for example by reference to the generated spectra and specifically when those spectra exhibit no change with increasing distance from the vessel walls or detecting the distance using a proximity detector or medical imaging device.

The spectral matrix of the unwanted signals is decomposed in step 412 to create the matrix operator P in step 414. In one embodiment, singular value decomposition (SVD) is performed on the spectral matrix X resulting in the T and P matrices, in step 412. The P matrix is then used to form the operator in Equation (4) in step 414. As discussed below, the obtained OSP unwanted spectral signature filters are used as a preprocessing method prior to the creation of the model. The application of the filter significantly improves the prediction ability of the final models or their accuracy in generating a discrimination or classification result from the analysis.

GLS Algorithm

The generalized least squares (GLS) regression method was developed more than 20 years ago by extending the ordinary least squares (OLS) and weighted least squares (WLS) for more general cases where the error terms in the models displayed a non-random uncertainty. The use of GLS as a pre-processing option in spectral data analysis was recently introduced. A priori knowledge was used to shrink or down-weight an unwanted signal prior to the application of multivariate calibration methods. This method can also be used to increase or up-weight a desired spectral signature and furthermore the two methods can be implemented together as a technique to up-weight a wanted signal then down-weight the unwanted signal, or vise versa all prior to the application of the multivariate analysis method or the machine learning method.

With reference to FIG. 5, the matrix Z only includes a priori spectra of the unwanted spectral signature contributing a signal to the overall spectrum. As with the OSP algorithm, and in a particular example, the spectra used in the matrix Z are collected from an "infinite" blood depth, in step 510, which is the same as step 410 in FIG. 4 discussed previously. Then, in step 512, the blood spectra are processed into the uncertainty covariance matrix A defined as:

$$A = Z^T Z/(m-1) + \alpha I \quad (6)$$

where m is the number of spectra in matrix Z, I is the identity matrix, and $\alpha$ is an adjustable small constant. $\alpha$ is added to insure that the covariance matrix is of full rank in order to do the math required. The amount of $\alpha$ added is calculated in step 514 for the case of the down-weighting matrix. The selected value is a balance between maximizing the down-weighting of the signal contributed from the unwanted signal, in this specific case, the blood absorbance, and minimizing the amount of white random noise from being up-weighted during the process (creating a noisier spectrum).

The full rank uncertainty covariance matrix $\Delta$ is then decomposed, in step 516, into a full rank component scores and vectors:

$$\Delta = U\Lambda V^T \quad (7)$$

where U is the matrix containing the scores, V is the matrix of the eigenvectors and $\Lambda$ is the eigenvalues produced from the decomposition process. The sum of the diagonal eigenvalues of the matrix $\Lambda$, is used to normalize the eigenvalues. The GLS operator G is then determined in step 518. It is defined as:

$$G = V\Lambda^{-1/2} V^T \quad (8)$$

The GLS operator uses only the eigenvectors obtained from the decomposition process of $\Delta$ from Equation (7) and reduces the influence of the eigenvectors by the scaled eigenvalues from Equation (8). The undesired spectral signature Z in Equation (1) will be eliminated by the application of operator G to the original spectral matrix X. If the unwanted spectral signal in Z can be entirely described by the uncertainty covariance matrix $\Delta$ from a priori knowledge then the original spectra can be corrected to:

$$X_{GLS} = GR + GE \quad (9)$$

On the other hand, as mentioned previously, instead of shrinking the unwanted spectral signal (in this case, blood or other intervening fluid), the characteristics of the spectra of interest are up-weighted in another implementation. The up-weighting is based on the same basic principles as the down-weighting GLS approach just discussed, however, the target or desired spectral signature is now used as a priori knowledge of the component of interest, such as the spectrum of vulnerable plaque or other contributors to high risk vulnerable plaque. Another embodiment of the application is to apply both the up-weighted and the down-weighted filter in any order to increase the optimized signal due to the high risk vulnerable plaque over that of the unwanted spectral signal.

Pattern Recognition Overview

Pattern recognition algorithms use mathematical models developed by modeling the relationship between the acquired spectra of something known, in this specific example, the chemical composition of known tissue samples. These models are typically based on large amounts of patient data or ex vivo data simulating in vivo spectral responses and data. The mathematical models can be based upon multivariate techniques such as PCA and PLS base algorithms along with other types of classification schemes, which use machine learning algorithms such as neural networks, fuzzy logic, or support vector machines.

In the use of PCA-based algorithms, a large number of wavelengths can be used to create a model. The PCA method reduces the spectral information to variations common to all of the spectra (called factors or latent variables) and a set of scalar amplitude values that are distinct to each spectrum (scores). These score values are used in the discriminate routine to separate different class grouping from one another. In some cases, only one classification group is needed to create the model, and it is this model that is used to determine how well it discriminates against all other sample classes both within and outside of the model classification group boundaries. For example, in one embodiment a single boundary PCA Model is created using for example the Mahalanobis distance calculation of the group mean of for example the LP samples used as the class model. Other tissue samples are used as validation tests: LP, FIB, CAL, and NML. In general a Mahalanobis distance of three (3) standard deviations can be used to exclude samples from the classification set but other values can be used to optimize the discrimination ability of the model. In other embodiments other screening tests are also applied to the data, involving the high and low score value and the maximum residual value from the model. In order for a sample to be assigned as part of the model group it must pass all three tests, the group Mahalanobis Distance, the Score and the Residual tests. In another embodiment the PCA matrix can include a column of the spectral residuals augmented to the matrix prior to the final analysis using Mahalanobis distance and/or including the other screening tests for the high and low score value and the maximum residual value from the model. In another embodiment the model can bypass the threshold method altogether and provide a map of the distribution of the values obtained from the group Mahalanobis Distance prediction.

Figure 6:
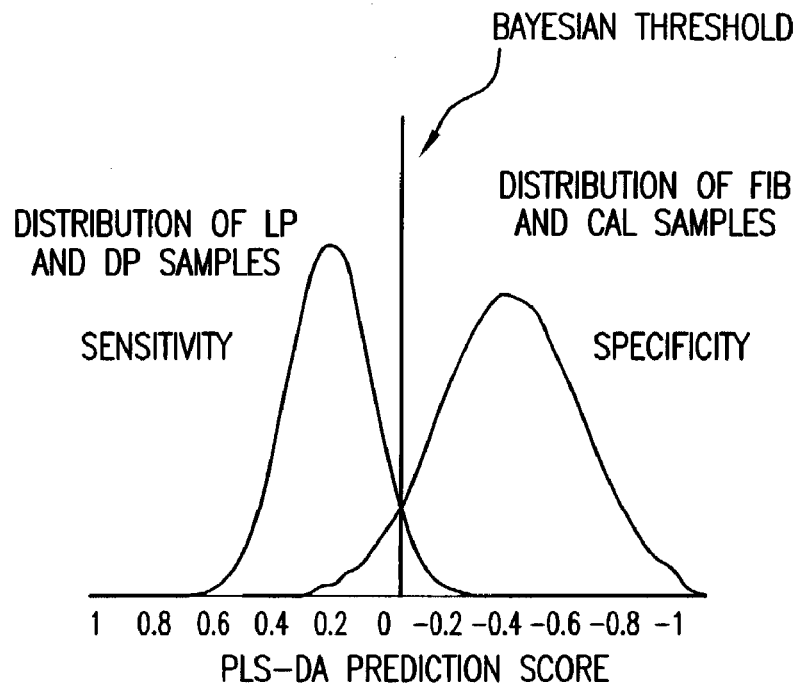
FIG. 6 is a plot of the result of the discrimination step as a function of the prediction score, illustrating a calibration model produced from the present invention.

With reference to FIG. 6, a calibration model based upon a multivariate regression technique is built distinguishing the differences between two classifications or other classification schemes of interest. In a current implementation, the regression technique used is PLS-DA. The PLS-DA model is based upon maximizing the separation of the information based upon the LP and DP groups from the information obtained from the FIB and CAL groups. A threshold is established by a classifier providing the mechanism for separating the LP and DP samples from all other groups or samples. The classifier can also provide the calculated results of the scores from the model, which can be used to provide the user with a gray-scale or color scale map.

In another embodiment, a calibration model based upon machine learning techniques is built distinguishing the differences between two classifications schemes, or more, of interest. The classification is provided by the application of the machine learning system approach that determines which combinations of the measurements are sufficient to distinguish between the classes. These methods can be applied as non-linear or linear separators. In one embodiment, artificial neural networks are used and the method is fine tuned by changing the number of degrees of freedom or dimensionality of the model. In another embodiment, support vector machines form hyper-planes between the assigned classes and in general attempt to maximize the separation between the two closest points in each classification group.

In current embodiment the PLS-DA algorithm is used. Once the spectra have been corrected for the unwanted influence of blood (step 112 in FIG. 3), the spectra are then separated into two classification groups, one with the LP and DP class spectra and the other with the FIB and CAL class spectra in step 114, according to one classification scheme. In another embodiment, the scheme distinguishes between vulnerable plaques or thin-cap fibroatheroma (TCFA) and non-vulnerable plaques or non-TCFA.

The core of the PLS-DA algorithm currently used is a spectral decomposition step performed via either the NIPALS (H. Wold, "Soft modeling by latent variables; the nonlinear iterative partial least squares approach." J. Gani, ed. *Perspectives in probability and statistics*, pp 520-540. Academic Press, London, 1975) or the SIMPLS (S. De Jong, *Chemom. Intell. Lab. Syst.*, 18(1993), 251-263) algorithm.

Figure 7:
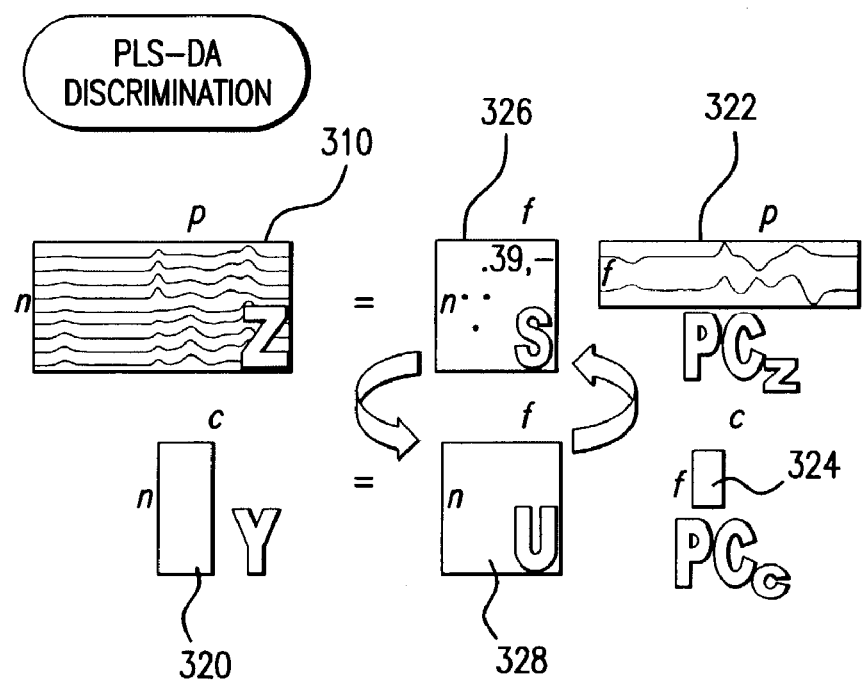
FIG. 7 is a diagram illustrating the use of nonlinear iterative partial least squares (NIPALS) decomposition of the spectral information used in the discrimination step, according to the present invention.

FIG. 7 is a diagram representing the NIPALS decomposition of the spectral information represented by the Z matrix 310 and the binary classification information represented by the Y matrix 320.

Z 310 is the spectra data matrix, Y 320 is the binary component information matrix, S and U are the resultant scores matrix 326, 328 from the spectral and component information respectively and PCz 322 and PCc 324 are the eigenvectors for the spectral and component information, respectively. The other nomenclature is for the number of spectra (n), the number of data points (p), the number of components (c), and the number of final principal components (f).

Once the first decomposition is made resulting in a latent variable and score for each of the Z and Y matrices, the resultant scores matrix for the spectral information (S) 326 is swapped with the scores matrix containing the binary classification information (U) 328. The principal component information from PCz and PCc 322, 324 are then subtracted from the Z and Y matrices 310, 320, respectively. These newly reduced matrices are then used to calculate the next latent variable and score for each round until enough PC are found to represent the data. Before each decomposition round, the new score matrices are swapped and the new PCs are removed from the reduced Z and Y matrix, The final number of latent variables arrived at from the PLS decomposition (see f) are highly correlated with the group classification information due to the swapped score matrices. The PCz and PCc matrices contain the highly correlated variation of the spectra with respect to the two groups used to build the model. The second set of matrices, S and U, contain the actual scores that represent the amount of each of the principle component variation that are present within each spectrum.

The scores from the S matrix are used to build the discrimination calibration model represented by FIG. 6. The threshold was set using the LP and DP scores for one group and the FIB and CAL scores for the other group according to one classification scheme for the blood vessels. For predictions, an unknown spectrum is decomposed to the same S matrix and if the score is above the threshold of the model then that sample is said to be either a member of the LP and/or DP class.

Parameter Optimization for Filter Development

As discussed above, both of the proposed unwanted spectral signal filters require a priori knowledge about the spectral contributions of the unwanted spectral signal, in this particular example, the blood variation. The OSP filter requires that the basis sets (or principal components) optimally span the orthogonal subspace using the simple assumption that the orthogonal projections will remove the signature of the unwanted signal due to, in this case blood. While the GLS algorithm is similar in outcome to the OSP filter, it differs with respect that all of the basis sets are retained in the model and a small adjustable parameter, which allows for downweighting the unwanted variation, is optimized while minimizing the white noise signature.

The spectra were obtained using a FOSS NIRSystems 6500 with an attached fiber optic Smart Probe. The probe was position above the tissue sample with blood intervening at sample-to-probe depth changing from 0.0 to 3.0 mm in 0.5 mm steps with one extra step positioned at 0.25 mm. A PLS-DA model was built using all the data at the various depths in the following examples for both the OSP and GLS filter. The lipid pool (LP) class and the disrupted plaque (DP) class spectra were both assigned to be part of the vulnerable plaque model (or sensitivity—SENS) and the fibrotic (FIB) class and the calcific (CAL) class spectra were not part of the model (or specificity—SPEC). The spectra were first preprocessed using SNV followed by the OSP or GLS filter using an infinite blood signature and then mean centering the data prior to the application of the PLS-DA algorithm or they were not preprocessed prior to the application of the OSP and GLS filters. The spectral range tested spanned from 1100 nm to 1350 nm in the NIR region.

In an effort to access how well the methods performed, the leave one out (LOO) cross-validation (CV) method of analysis was used. From the LOO-CV prediction results, a figure of merit (FOM) used to assess the performance of the PLS-DA models was created using the mean Euclidean Distance (ED) equation. The results were calculated from the differences between the analysis prediction using LOO-CV of the classes representing the vulnerable plaque model or SENS and the classes not representing the model or SPEC to those values representing a perfect model prediction of 100% SENS and 100% SPEC.

$$ED_{FOM} = 1 - \sqrt{\frac{\sum_{x=1}^{N} (1 - SENSx)^2 + \sum_{x=1}^{M} (1 - SPECx)^2}{(N+M)}} \quad (10)$$

where N is the number of classes that are included in the model and M is the number of classes that are not part of the model, and the (1) in the square root equation represents the 100% perfect prediction results. For a perfect prediction model, the $ED_{FOM}$ is 1 and for a completely divergent model the $ED_{FOM}$ is 0.

Determination of OSP Subspace Projection Dimension

In the development of the OSP blood filters, the dimension of the OSP subspace should be optimized. For long pathlength samples, the blood signature dominates the spectra. If the OSP filter was not optimized then it would be easy to inadvertently remove the target tissue signal.

Examples of the OSP filters were calculated here using from zero to 5 principal components (PCs), which is the basis set of the projection into the subspace of the data matrix. The data were first preprocessed using the SNV algorithm prior to the application of the OSP filter then the data are mean centered (MC). The 0-dimension OSP filter is the preprocessing results obtained from the SNV+MC method alone. The mean $ED_{FOM}$ calculated from the differences between the analysis prediction for each of the SENS and SPEC values and 100% prediction was used to assess PLS-DA models.

The results are presented in Table I where the columns of the table represent the number of latent variables (LVs) used to build each of the PLS-DA models, while the rows correspond to the basis set dimensions or PCs used in OSP filters.

TABLE I

SNV + OSP + MC $ED_{FOM}$ Predictions for PLD-DA Models

| LVs in PLS-DA | | 1 | 2 | 3 | 4 | 5 | 6 | 7 | 8 |
|---|---|---|---|---|---|---|---|---|---|
| OSP | 0 | 0.4551 | 0.6189 | 0.6632 | 0.6727 | 0.7427 | 0.7482 | 0.7691 | 0.7659 |
| PCs | 1 | 0.5639 | 0.6122 | 0.6819 | 0.7913 | 0.7964 | 0.7677 | 0.7282 | 0.7162 |

TABLE I-continued

SNV + OSP + MC $ED_{FOM}$ Predictions for PLD-DA Models

| LVs in PLS-DA | 1 | 2 | 3 | 4 | 5 | 6 | 7 | 8 |
|---|---|---|---|---|---|---|---|---|
| 2 | 0.6678 | 0.6257 | 0.7929 | 0.7889 | 0.7675 | 0.7446 | 0.7184 | 0.7535 |
| 3 | 0.6695 | 0.6767 | 0.8045 | 0.7842 | 0.7410 | 0.7127 | 0.7576 | 0.7500 |
| 4 | 0.6483 | 0.6858 | 0.8030 | 0.7446 | 0.7365 | 0.7396 | 0.7507 | 0.7517 |
| 5 | 0.6559 | 0.6280 | 0.7129 | 0.7319 | 0.6877 | 0.7485 | 0.7662 | 0.7738 |

From the table it is seen that by increasing the basis set dimension of the OSP subspace more undesired variation was removed creating a less complicated model. The use of the OSP filter improved the PLS-DA model both in terms of the mean $ED_{FOM}$ and in the decrease in the number of latent valuables (see bold numbers in the table) needed to build the model. The best prediction results seemed to center near 3 PCs in the OSP space and 3 LVs in the PLS-DA model with a mean $ED_{FOM}$ of 0.8045. In almost all cases of the PLS-DA LVs tested from 1 to 8, the model was improved by the additional step of applying the OSP filter.

Optimization of α for GLS Filter

Like OSP, in one embodiment, the GLS filter attempts to suppress the spectral features due to blood while attempting to improve upon the target signal (lipid pool). The small constant, α in equation 6, is the only adjustable parameter for the GLS filter. As discussed above, a constant was added to the diagonal of the uncertainty covariance matrix, Δ. The adjustment of α changes the magnitude of the unwanted variation within the matrix and is optimized providing the down-weighting of the unwanted spectral signal, in this example the infinite spectra of blood.

In order to simplify the problem of assessing the unwanted spectra signal level and save computation time, a universal constant is used, defined by the uncertainty covariance matrix according to $$\alpha = \sigma^2/\alpha' \quad (11)$$

where $\sigma^2$ is the variance of the uncertainty covariance matrix and α' is an adjustable number, such as 1, ... 50, ..., 100, ..., 200, ..., ∞.

The spectral data and PLS-DA model assessment was the same as that used in the OSP section. The spectra were preprocessed using SNV followed by the application of the GLS filter using an infinite blood signature and then the data was mean centered (MC). The assessment was based upon the $ED_{FOM}$ obtained from the prediction results.

In the first example below the GLS filters were optimized using the variable α' and assessing the value of the $ED_{FOM}$ of the resultant PLS-DA models. The results are listed in Table II. Like the OSP optimization process, the data were first preprocessed using the SNV algorithm prior to the application of the GLS down weighting filter then finally the data were MC. The notation of α'=0 is used only to represent the situation of the preprocessing results from the SNV+MC method alone. The columns of the table represent the number of latent variables used in PLS-DA models, while the rows correspond to the GLS filter with the adjustable parameter α calculated with increasing values of α'.

TABLE II

SNV + GLS + MC $ED_{FOM}$ Predictions for PLD-DA Models via Optimization of α

| | LVs in PLS-DA | 1 | 2 | 3 | 4 | 5 | 6 | 7 | 8 |
|---|---|---|---|---|---|---|---|---|---|
| GLS $\sigma^2/\alpha'$ | α' = 0 | 0.4551 | 0.6189 | 0.6632 | 0.6727 | 0.7427 | 0.7482 | 0.7691 | 0.7659 |
| | 10 | 0.6585 | 0.6236 | 0.7313 | 0.7699 | 0.7634 | 0.7702 | 0.7522 | 0.7644 |
| | 50 | 0.6571 | 0.6250 | 0.7694 | 0.7436 | 0.7805 | 0.7689 | 0.7543 | 0.7579 |
| | 100 | 0.6516 | 0.6292 | 0.7732 | 0.7455 | 0.7892 | 0.7714 | 0.7515 | 0.7558 |
| | 150 | 0.6535 | 0.6325 | 0.7733 | 0.7491 | 0.7905 | 0.7654 | 0.7521 | 0.7515 |
| | 175 | 0.6531 | 0.6337 | 0.7683 | 0.7491 | 0.7954 | 0.7655 | 0.7506 | 0.7513 |
| | 200 | 0.6529 | 0.6366 | 0.7675 | 0.7515 | 0.7939 | 0.7631 | 0.7497 | 0.7480 |
| | 250 | 0.6459 | 0.6355 | 0.7665 | 0.7530 | 0.7926 | 0.7616 | 0.7516 | 0.7425 |
| | 300 | 0.6447 | 0.6350 | 0.7654 | 0.7530 | 0.7811 | 0.7542 | 0.7519 | 0.7485 |
| | ∞ | 0.6255 | 0.7429 | 0.7513 | 0.7530 | 0.7435 | 0.7573 | 0.7674 | 0.7532 |

It can be seen from Table II that the application of the GLS filter simplified the discrimination model by two LV from 7 down to 5 where the optimal value for α' is found to be approximately 175. This decease in LV with the increase in α' produces an increase in the $ED_{FOM}$ of about 0.03 which equates to a mean prediction increase of 3%. The optimized value of α' is then fixed in the rest of the analyses that are reported here. While α' is fixed for this data set at a value of 175, any future analysis using different tissue samples would require α' to be re-optimized.

Improvement of Discrimination Power for PLS-DA

As defined earlier, the discrimination power of a model is based on two features: one concerning the increase of sensitivity and specificity the other the extension of the discrimination depth or pathlength in this specific case, through blood. By using the preprocessing methods discussed above both features have been improved. The improvement of the PLS-DA model as a function of the extension of the discrimination depth or pathlength is demonstrated within this section.

OSP Filter

Referring to the first row in Table I, no OSP filter and only SNV+MC preprocessing, the maximum prediction results was 0.7671 from the LOO-CV $ED_{FOM}$ using 7 LVs in the PLS-DA model. The addition of the OSP filter increased the maximum value of the mean $ED_{FOM}$ to 0.8045, decreasing the PLS-DA model LVs to 3 when 3 PCs were used to build the OSP filter. With the addition of the OSP filter the total sensitivity and specificity of the PLS-DA model was increased by about 5%.

While the LOO-CV $ED_{FOM}$ results from above provided a measurement tool to assess each model on a global scale for comparisons, they did not indicate how the model will perform with respect to the sample-to-probe depths. This is important since in some embodiments the catheter is free to move within the artery, therefore the greater the prediction at the higher sample-to-probe depths, the better the model.

In the next case, the PLS-DA model is assessed with respect to each of the sample-to-probe depths and is tabulated over all of the blood depths in Table III. The columns of the table are the sample-to-probe depth changes from 0.0 to 3.0 mm with the last row indicating the optimized LV used in the PLS-DA model. The rows represent the results from the optimized PLS-DA prediction using either no OSP filter (0 PC) or 1 to 3 PCs. From the table, the improvement in the ability to discriminate the classes as the sample-to-probe depth is increased, is significant. The model selected as the best performing OSP filter outperformed the SNV+MC model, i.e., without pre-OSP filtering, by about 18% at depths greater than 1.5 mm.

TABLE III

Mean $ED_{FOM}$ Results Using the Best PLS-DA and OSP Filters Over the Full Sample-to-Probe Depth Range.

| | | \multicolumn{8}{c}{Depth (mm)} | LVs in |
|---|---|---|---|---|---|---|---|---|---|---|
| | | 0.0 | 0.25 | 0.5 | 1.0 | 1.5 | 2.0 | 2.5 | 3.0 | PLS-DA |
| OSP PCs | 0 | 0.8321 | 0.8228 | 0.8390 | 0.8321 | 0.8188 | 0.7265 | 0.6562 | 0.6251 | 7 |
| | 1 | 0.8310 | 0.8287 | 0.8287 | 0.8394 | 0.8283 | 0.7673 | 0.7353 | 0.7124 | 5 |
| | 2 | 0.8020 | 0.8001 | 0.8287 | 0.8244 | 0.8244 | 0.8076 | 0.7584 | 0.6975 | 3 |
| | 3 | 0.8244 | 0.8244 | 0.8455 | 0.8228 | 0.8206 | 0.7921 | 0.7693 | 0.7371 | 3 |
| | 4 | 0.8165 | 0.8287 | 0.8455 | 0.8228 | 0.8287 | 0.8022 | 0.7742 | 0.7053 | 3 |
| | 5 | 0.8612 | 0.8342 | 0.8248 | 0.8102 | 0.7903 | 0.7588 | 0.6897 | 0.6210 | 8 |

The best PLS-DA model for the OSP filtered data, using the $ED_{FOM}$, was found to be 3 PCs and 3 LVs and without using an OSP filter, 7 LVs. These two models are further examined by using the plot of the ROC-AUC which provides another assessment method on the ability of the model to separate the two class groups (LP and DP versus FIB and CAL). The ROC-AUC can be assessed by determining the area under the curve of all the prediction results and that the discrimination power can be assigned as follows:

| Excellent = | 1.0 to 0.9 |
|---|---|
| Good = | 9.0 to 8.0 |
| Fair = | 0.8 to 0.7 |
| Poor = | 0.7 to 0.6 |
| Failed = | 0.6 to 0.5 |

Figure 8:
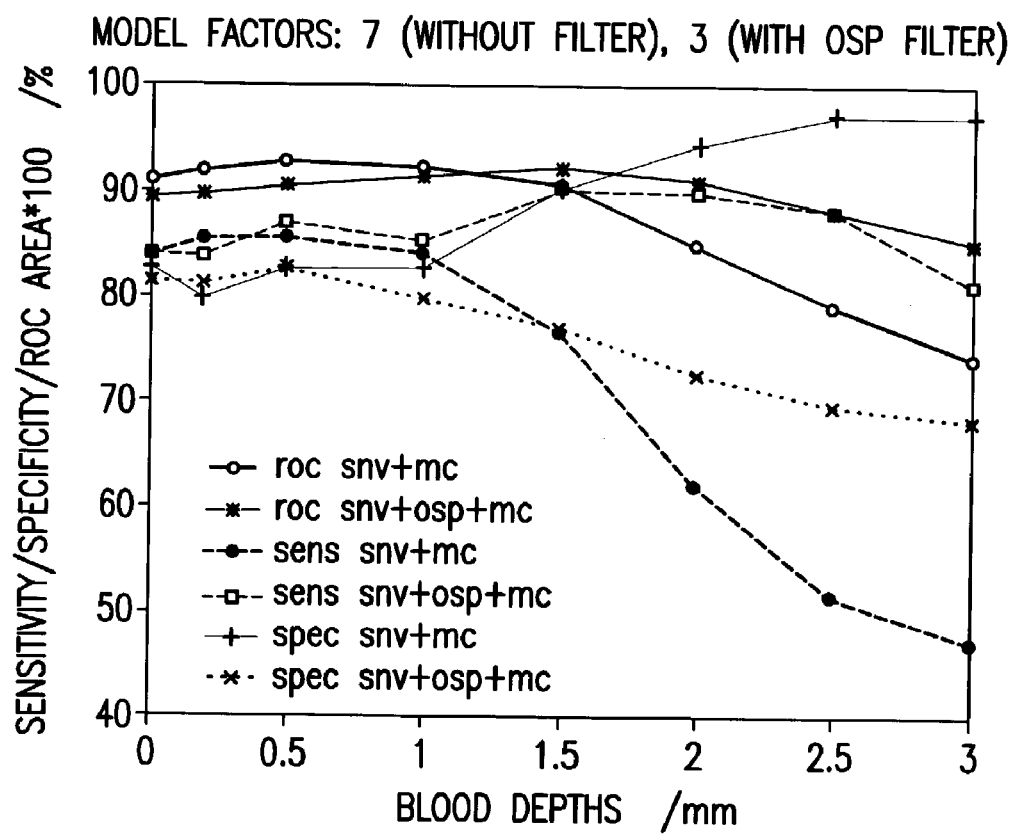
FIG. 8 is a plot in which the X-axis is the Blood Depths in millimeters (mm) and the Y-axis is one of the following.

The plot in FIG. 8 shows the ROC-AUC values across all of the sample-to-probe or Blood Depths for the model without the filter (SNV+MC) as a solid line with open circles and the OSP filtered data as a solid line with star symbols. It is seen that the ROC-AUC has been significantly improved by the addition of the OSP filter. The addition of the filter improved the results significantly, for instance, at the blood depth of 3.0 mm, the ROC-AUC was 0.74 for the unfiltered data (SNV+MC) and 0.85 for the filtered model (SNV+OSP+MC). The ROC-AUC number indicates the ability of the two classes to be separated from each other in the prediction score space. From the scale listed above for the ROC-AUC values, it indicates that the SNV+MC model can provide a FAIR model but by the addition of the OSP filter the model is GOOD all the way out to 3.0 mm depths.

FIG. 8 additionally displays the prediction results separately as SENS and SPEC. The dotted lines show the sensitivities over blood depth with the OSP filter and without, while the dashed lines are specificities with the OSP filter and without. The unfiltered model prediction of the SENS (dashed line solid circle) and SPEC (dot-dash line with plus) results diverge dramatically as you increasing the sample-to-probe or blood depth greater than 1 mm, indicating that the model lost the ability to discriminate between the two classes. However, by adding the OSP filter the divergence decreased significantly (SENS—dashed line with open square and SPEC—dashed line with *). At the 3.0 mm depth the sensitivity obtained using SNV+OSP+MC model was at 82% with a corresponding specificity of 68% indicating the ability of the OSP filtered model to discriminate.

In an effort to understand why the OSP filter improves the model, that actual prediction scores for each of the sample-to-probe depths were plotted as histograms in FIG. 9. The distributions of prediction scores for the two classes (LP and DP versus CAL and FIB) were plotted separately at each sample-to-probe separation or blood depth moving from top to bottom of FIG. 9.

Column one in FIG. 9 is the results from SNV+MC (no OSP filter), column two is the results of the OSP filter and column three is the ROC results for both models. The X-axis for columns one and two are the prediction scores of PLS-DA model with positive scores on the left side of the axis and column three is the prediction results of 1 -Specificity. The Y-axis of columns one and two correspond to the probability/ frequency of the prediction scores and for column three is the prediction results of the model Sensitivity. The rows in FIG. 9 are for each sample-to-probe separation or blood depth, increasing from top to bottom from 0.0 mm to 3.0 mm.

From FIG. 9 column one, as the depth of the sample-to-probe separation increases, a negative bias in prediction score is observed for the model without the OSP filter. The results is a poor discrimination after a blood depth of 1.0 mm, observed by the prediction scores representing the SENS moving to the right side of the fixed threshold (vertical black line in the figure). By applying the OSP filter (column two), the bias was dramatically reduced resulting in the model capable of prediction at large blood depths.

The ROC analysis was conducted for each blood depth (see column three in FIG. 9). The plots of 1-Specificity vs. Sensitivity are plotted for each blood depths. The solid lines in the figure are the curves obtained without the use of the OSP filter, while the dashed lines are the results using the OSP filter. It appears from the figure that the OSP filter can efficiently remove the blood variation and significantly separate the two distributions through 3.0 mm of blood, leading to an average increase in the ROC-AUC of 18% at blood depths above 1.5 mm (as seen by the results in FIG. 8).

GLS Filter

The same analysis described above has been applied to the GLS filter with the PLS-DA LOO-CV model results assessed using $ED_{FOM}$. Table IV displays the $ED_{FOM}$ discrimination results of the PLS-DA models combined with the GLS filter over all blood depths. The columns in Table IV are the sample-to-probe depth changes from 0.0 to 3.0 mm with the last column the optimal LV that was used to build each of the PLS-DA models. The rows represent the results from the PLS-DA prediction using either no GLS filter ($\alpha'=0$) or with the GLS filter using an $\alpha'>10$. From the table, the improvement in the ability to discriminate groups as the sample-to-probe depth is increased, is again significant. The model selected as the best performing GLS filter outperformed the SNV+MC model by about 18% at depths greater than 1.5 mm.

rately in FIG. 10, for data preprocessed by SNV+MC or by SNV+GLS+MC. The ROC-AUC increased somewhat at depths>2.0 mm when GLS down-weighting was applied. As was the case for the OSP filter, the ROC-AUC has improved by the addition of the GLS filter. For instance, at the blood depth of 3.0 mm, the ROC-AUC was increased from 0.75 (SNV+MC) to 0.80 (SNV+GLS+MC), implying that a GOOD model can be expected at 3.0 mm depths after GLS filtering.

FIG. 10 also plots the prediction results of the SENS and SPEC separately. The model prediction without GLS for the SENS (dashed line solid circle) and SPEC (dot-dash line with plus) are the same as was seen in FIG. 8 and again the results diverge dramatically with increasing sample-to-probe distance or blood depth greater than 1 mm, indicating that the model lost the ability to discriminate between the two classes. However, by adding the GLS filter the divergence decreased significantly (SENS—dashed line with open square and SPEC—dashed line with *). At the 3.0 mm depth the sensitivity obtained using SNV+GLS+MC was near 75% with a corresponding specificity of 70% indicating the increased ability of those models using the GLS filter model to discriminate better than those without the GLS filter.

The same type of plot as that shown in FIG. 9 is shown here for the GLS filtered data. A plot of the response of the distributions of the predictions scores for the data without and with the use of the GLS filter is shown in FIG. 11 in column one and column two respectively. Column three is the ROC for the models without the GLS filter and with the GLS filters. The rows of FIG. 11 are the sample-to-probe separation depths that span the range from 0.0 to 3.0 mm.

Comparison Between OSP and GLS Filters

Both OSP and GLS filters have demonstrated the ability of correcting the undesired variation of an unwanted spectral signal, in this specific case, a blood spectrum. As discussed above, the OSP filter blocks the spectral features that are correlated to the undesired information according to a priori knowledge. In other words, only the spectral features that are orthogonal to the undesired information can pass the filter.

TABLE IV

Mean $ED_{FOM}$ over blood depth (mm) for the best PLS-DA models with GLS filter

| | | Depth (mm) | | | | | | | | LVs in PLS- |
|---|---|---|---|---|---|---|---|---|---|---|
| | | 0.0 | 0.25 | 0.5 | 1.0 | 1.5 | 2.0 | 2.5 | 3.0 | DA |
| GLS | $\alpha' = 0$ | 0.8321 | 0.8228 | 0.8390 | 0.8321 | 0.8188 | 0.7265 | 0.6562 | 0.6251 | 7 |
| $\sigma^2/$ | 10 | 0.8321 | 0.8228 | 0.8455 | 0.8321 | 0.8226 | 0.7265 | 0.6555 | 0.6244 | 6 |
| $\alpha'$ | 50 | 0.8244 | 0.8372 | 0.8390 | 0.8304 | 0.7931 | 0.7437 | 0.7011 | 0.6749 | 5 |
| | 100 | 0.8165 | 0.8342 | 0.8287 | 0.8240 | 0.7681 | 0.7218 | 0.7061 | 5 | |
| | 150 | 0.8228 | 0.8342 | 0.8200 | 0.8248 | 0.8145 | 0.7584 | 0.7414 | 0.7080 | 5 |
| | 175 | 0.8228 | 0.8342 | 0.8200 | 0.8248 | 0.8238 | 0.7584 | 0.7432 | 0.7360 | 5 |
| | 200 | 0.8228 | 0.8342 | 0.8200 | 0.8248 | 0.8238 | 0.7584 | 0.7443 | 0.7230 | 5 |
| | 250 | 0.8084 | 0.8342 | 0.8200 | 0.8248 | 0.8188 | 0.7703 | 0.7584 | 0.7058 | 5 |
| | 300 | 0.8084 | 0.8252 | 0.8200 | 0.8318 | 0.8188 | 0.7723 | 0.7424 | 0.6299 | 5 |

The best GLS filter model (bold row in Table IV) was used for further analysis in this section (PLS-DA using 5 LVs and the GLS filter using $\alpha'$ of 175).

The plot in FIG. 10 shows the ROC-AUC values across all of the sample-to-probe or Blood Depths for the model without the filter (SNV+MC) as a solid line with open circles and the GLS filtered data as a solid line with star symbols. The Sensitivity and Specificity for the ROC are illustrated sepa- The desired features, if they are statistically related to the undesired background, will also be blocked by the filter. GLS preprocessing is based on a different principle. It weights the undesired information down and emphasizes the desired information (or vise versa in the case of the up-weighted method).

Unwanted Signal Variability

The undesired spectral signal can be obtained in many different ways, including the use of a priori knowledge. Using the specific case above with blood as the unwanted spectral signal, one embodiment is to collect multitudes of blood samples ex vivo and obtain the spectrum of each with tissue within the spectral illumination spot but held at a distance that no spectra changes occur with further separation. Other embodiments would allow for any distance from the tissue to be used and any tissue sample. An in vivo embodiment would allow for the acquisition of unwanted spectrum from within the patient at a site that provides a signal that is unchanging. A further in vivo embodiment would be to acquire the spectrum of blood with tissue backing using tissue (such as normal or relatively free from diseased) as the unwanted signal. Any blood depth can be used. Other methods can be used by those familiar with the technique.

Another embodiment uses a container that can hold the blood sample. In this embodiment there is no tissue in the spectral illumination area. There are many other methods that are not discussed here as this is meant only as an example of the attainment of an unwanted spectral signal. As discussed in the summary the principles and features of this invention may be employed in various and numerous embodiments without departing from the scope of the invention. The unwanted spectral signal may be in particular blood or in general any undesired spectral signal that impedes the assessment of the blood vessel walls.

Preprocessing

Due to the variability of the system, it is necessary to preprocess the data prior to analysis to correct for scatter or bias. For example a few different methods were tested and are illustrated below in Table V showing the progression of the model performance as the preprocessing method is changed. GLS and OSP were compared with other preprocessing methods such as standard normal variate (SNV), mean centering (MC), Savitsky-Golay smoothing and differentiation (Der1 and Der2 for first and second derivative respectively), multiplicative scatter correction (MSC), finite impulse response filters (FIR) and autoscaling (AUTO) over the spectral range from 1100 to 1350 nm to determine the best models. The latent variables used to create the best PLS-DA model were determined according to the LOO cross-validation technique.

Table V shows the cross-validation prediction results for the preprocessing methods investigated. The results are displayed as a function of prediction depth with column one containing all the prediction depths from 0.0 to 3.0 mm and the other columns representing each of the depths as 0.0, 0.25, 0.5, 1.0, 1.5, 2.0, 2.5, and 3.0 mm for the sample-to-probe separation depths.

TABLE V

Mean $ED_{FOM}$ Comparing Preprocessing Methods and Probe Depths (1100 to 1350 nm)

| | Depth (mm) | | | | | | | | LVs in PLSDA |
|---|---|---|---|---|---|---|---|---|---|
| | 0.0 to 3.0 | 0.0 | 0.25 | 0.5 | 1.0 | 1.5 | 2.0 | 2.5 | 3.0 | |
| MC | 0.7508 | 0.7953 | 0.8022 | 0.8287 | 0.8385 | 0.7757 | 0.7060 | 0.6451 | 0.6151 | 8 |
| SNV + MC | 0.7691 | 0.8321 | 0.8228 | 0.8390 | 0.8321 | 0.8188 | 0.7265 | 0.6562 | 0.6251 | 7 |
| GLS (175) + MC* | 0.7634 | 0.8058 | 0.8112 | 0.8228 | 0.8188 | 0.7656 | 0.7262 | 0.6798 | 0.6771 | 8 |
| SNV + GLS (175) + MC* | 0.7954 | 0.8228 | 0.8342 | 0.8200 | 0.8248 | 0.8238 | 0.7584 | 0.7432 | 0.7360 | 5 |
| OSP (3) + MC* | 0.7666 | 0.8429 | 0.8482 | 0.8482 | 0.8014 | 0.7858 | 0.7329 | 0.6683 | 0.6055 | 6 |
| SNV + OSP (3) + MC* | 0.8045 | 0.8244 | 0.8244 | 0.8455 | 0.8228 | 0.8206 | 0.7921 | 0.7693 | 0.7371 | 3 |
| Der1 + MC** | 0.7549 | 0.8228 | 0.8228 | 0.8228 | 0.8377 | 0.7692 | 0.7001 | 0.6633 | 0.6001 | 7 |
| Der2 + MC** | 0.7459 | 0.8390 | 0.8112 | 0.8144 | 0.8102 | 0.7880 | 0.6820 | 0.6309 | 0.5912 | 5 |
| AUTO + MC | 0.7627 | 0.8058 | 0.8200 | 0.8228 | 0.8277 | 0.7656 | 0.7303 | 0.6683 | 0.6607 | 9 |
| MSC + MC | 0.7908 | 0.8394 | 0.8245 | 0.8394 | 0.8240 | 0.8175 | 0.7622 | 0.7182 | 0.7007 | 7 |
| FIR + MC | 0.7552 | 0.8244 | 0.8287 | 0.8161 | 0.8094 | 0.7701 | 0.7024 | 0.6596 | 0.6309 | 8 |

*Number in the parentheses is the parameter used in the blood filter
**Der1 and Der2 use Savitsky-Golay smoothing and differentiation of 5 points This specific example shows that the addition of first removing the overall spectral offset and scatter in this specific case, using the SNV algorithm, prior to the application of the unwanted signal filter (SNV+OSP+MC or SNV+GLS+MC) significantly outperformed all preprocessing methods shown including the OSP and GLS filter alone. The preprocessing methods of GLS and OSP assume that the unwanted spectral signals to be processed are similar with respect to the variation along the y axis (absorbance). Since there will be variation in the amount of blood intervening between the probe and the target tissue sample, the signals in this case are not stationary along the y-axis. By including preprocessing methods prior to the formation of the unwanted signal filter, most of the variation caused by spectral influences such as scatter and bias can be minimized along the y-axis (see FIG. 13).

The table and descriptions are meant only as an example of how preprocessing the data prior to the application of the unwanted spectral signal can improve the model. It is not meant to capture all the modes of variation that are found nor is it meant to capture all of the methods that can be used to minimize or remove the effects that are not minimized by the application of the OSP or GLS filter.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for analyzing blood vessels in the presence of intervening unwanted spectral signal, the method comprising:

irradiating blood vessel walls through intervening fluid;
   collecting spectral responses;

determining spectral responses of the blood vessel walls from the collected spectral responses by applying a filter generated using a spectral response of the intervening fluid to remove or deemphasize a contribution of the intervening fluid relative to a signal from the blood vessel walls; and assessing states of the blood vessel walls in response to the determined spectral responses of the blood vessel walls.

2. A method as claimed in claim 1, wherein the step of irradiating comprises illuminating the blood vessel walls with an optical source.

3. A method as claimed in claim 2, wherein the optical source generates near infrared light.

4. A method as claimed in claim 1, wherein the step of collecting the spectral responses comprises detecting returning radiation to a catheter head.

5. A method as claimed in claim 1, wherein the spectral response of the intervening fluid is collected at a relatively large distance from the blood vessel walls.

6. A method as claimed in claim 1, wherein the spectral response of the intervening fluid is collected in a reference well, ex vivo.

7. A method as claimed in claim 1, wherein the filter is based on a generalized least squares analysis.

8. A method as claimed in claim 7, wherein parameters of the generalized least squares filter are optimized by analyzing a performance of the filter in improving an accuracy of a qualification analysis, such as a discrimination or classification, or a quantitative analysis.

9. A method as claimed in claim 1, wherein the filter is based on an orthogonal subspace projection analysis.

10. A method as claimed in claim 9, wherein a subspace projection dimension of the filter is optimized by analyzing a performance of the filter in improving an accuracy of a qualification analysis, such as a discrimination or classification process, or a quantitative analysis.

11. A method as claimed in claim 1, wherein the intervening fluid is blood.

12. A method as claimed in claim 1, wherein the intervening fluid is a fluid used to flush blood along a path to the blood vessel walls.

13. A method as claimed in claim 1, wherein the spectral response of the intervening fluid is determined from blood samples of multiple individuals.

14. A method as claimed in claim 1, wherein the spectral response of the intervening fluid is determined from blood samples of the current patient.

15. A method as claimed in claim 1, wherein the spectral response of the intervening fluid is determined from blood samples of the current patient and other individuals.

16. A method as claimed in claim 1, wherein the spectral response of the intervening fluid is determined by gathering a spectral response of a contrast agent.

17. A method as claimed in claim 1, wherein the spectral response of the intervening fluid is determined by gathering a spectral response of an artificial blood.

18. A method as claimed in claim 1, wherein the spectral response of the intervening fluid is determined by gathering a spectral response of a flushing agent such as saline solution.

19. A method as claimed in claim 1, wherein the spectral response of the intervening fluid is determined by gathering a spectral response of a fluid, such as a gas or liquid, that is used to expand a balloon catheter.

20. A method as claimed in claim 1, wherein the step of assessing states of the blood vessel walls in response to the determined spectral responses of the blood vessel walls comprises determining whether the blood vessel walls are comprised of vulnerable or non-vulnerable plaques.

21. A method as claimed in claim 1, wherein the step of assessing states of the blood vessel walls in response to the determined spectral responses of the blood vessel walls comprises determining whether the blood vessel walls are comprised of atheromas or normal tissue.

22. A method as claimed in claim 1, wherein the step of assessing states of the blood vessel walls in response to the determined spectral responses of the blood vessel walls comprises applying multivariate regression techniques.

23. A method as claimed in claim 1, wherein the step of assessing states of the blood vessel walls in response to the determined spectral responses of the blood vessel walls comprises classifying a state of the vessel walls.

24. A method as claimed in claim 1, wherein the step of assessing states of the blood vessel walls in response to the determined spectral responses of the blood vessel walls comprises relating the determined spectral responses with spectral responses of vessel walls in a state of interest.

25. A method as claimed in claim 1, wherein the step of assessing states of the blood vessel walls in response to the determined spectral responses of the blood vessel walls comprises classifying states of the vessel walls by relating the determined spectral responses with spectral responses of vessels walls in different states.

26. A method as claimed in claim 1, wherein the step of determining the spectral responses of the blood vessels walls comprises processing the collected spectra, being a composite of the intervening fluid and blood vessel walls, in an analyzer after detection of the collected spectral responses to remove or deemphasize the contribution of the intervening fluid.

27. A system for analyzing blood vessels in the presence of intervening fluid, the system comprising:
a source of radiation;
a catheter for directing the radiation at blood vessel walls through intervening fluid and collecting radiation from the blood vessel walls;
a detector system of monitoring the collected radiation;
a controller for generating spectral responses from the collected radiation detected by the detector system;
an analyzer for determining spectral responses of the blood vessel walls from the collected spectral responses from the controller and generating information for assessment of the blood vessel walls in response to the determined spectral responses of the blood vessel walls, wherein the analyzer determines the spectral responses of the blood vessel walls by applying a filter generated in response to spectra of the fluid to remove a contribution of the fluid.

28. A system as claimed in claim 27, wherein the source comprises an optical source.

29. A system as claimed in claim 27, wherein the source comprises a near infrared source.

30. A system as claimed in claim 27, wherein the spectra of the fluid is collected when a head of the catheter is at a relatively large distance from the blood vessel walls.

31. A system as claimed in claim 27, wherein the spectra of the fluid is collected in a reference well, ex vivo.

32. A system as claimed in claim 27, wherein the filter is based on a generalized least squares analysis.

33. A system as claimed in claim 32, wherein parameters of the generalized least squares filter are optimized by analyzing a performance of the filter in improving the assessment of a state of the blood vessel walls by the analyzer.

34. A system as claimed in claim 27, wherein the filter is based on an orthogonal subspace projection analysis.

35. A system as claimed in claim 34, wherein a subspace projection dimension of the filter is optimized by analyzing a performance of the filter in improving an accuracy of a discrimination process.

36. A system as claimed in claim 27, wherein the analyzer assesses states of the blood vessel walls in response to the determined spectral responses of the blood vessel walls by determining whether the blood vessel walls is comprised of vulnerable or non-vulnerable plaques.

37. A system as claimed in claim 27, wherein the analyzer assesses states of the blood vessel walls in response to the determined spectral responses of the blood vessel walls by determining whether the blood vessel walls are comprised of atheromas or normal tissue.

38. A system as claimed in claim 27, wherein the analyzer assesses states of the blood vessel walls in response to the determined spectral responses of the blood vessel walls by applying multivariate regression techniques.

39. A system as claimed in claim 27, wherein the analyzer provides a quantitative assessment of the blood vessel walls to an operator.

40. A system as claimed in claim 27, wherein the analyzer assesses states of the blood vessel walls in response to the determined spectral responses of the blood vessel walls by relating the determined spectral responses with spectral responses of vessels walls in different states.

41. A method for de-emphasizing a blood response in a spectral response of a structure of interest, the method comprising:
generating a filter determined by spectra representing a response of the blood which is collected at a relatively large distance from the structure of interest through the blood; and
applying the filter to a collected spectral response including the blood response to generate the spectral response of the structure of interest.

42. A system for spectrally analyzing interior structures of animals in the presence of unwanted spectral signal sources, the system comprising:
a source of radiation;
a catheter for directing the radiation at the interior structures through intervening medium and collecting radiation returning from the interior structures;
detector system of monitoring radiation from the interior structures;
a spectrometer controller for generating spectral responses from the monitored radiation detected by the detector system;
an analyzer for determining spectral responses of the interior structures from the generated spectral responses from the spectrometer controller by removing a contribution of the medium by applying a filter generated using a spectral response of the medium to remove or deemphasize a contribution of the medium relative to a signal from the interior structures and generating an assessment of a state of the internal structures in response to the determined spectral responses of the internal structures.

43. A blood vessel analysis method comprising:
collecting spectral responses of the blood vessels, the spectral responses including unwanted spectral signals caused by irradiating the blood vessel through an intervening fluid;
processing the spectral responses by applying a filter generated from the unwanted spectral signals to reduce the unwanted spectral signals relative to the blood vessel responses to generate determined spectral responses of the blood vessels; and
using the determined spectral responses to analyze the blood vessels.

44. A method as claimed in claim 43, wherein the step of collecting comprises irradiating the blood vessels with optical radiation.

45. A method as claimed in claim 43, wherein the step of collecting comprises irradiating the blood vessels with near infrared radiation.

46. A method as claimed in claim 43, further comprising processing the spectral responses to remove offsets and/or slopes.

47. A method as claimed in claim 43, further comprising processing the spectral responses to eliminate sources of variation of the signal not related to signal of interest.

48. A method as claimed in claim 43, further comprising processing the spectral responses by normalizing and/or autoscaling.

49. A method as claimed in claim 43, further comprising processing the spectral responses to enhance the spectral signal.

50. A method as claimed in claim 43, further comprising processing the spectral responses by mean centering the responses.

51. A method as claimed in claim 43, further comprising processing the spectral responses by detrending the responses.

52. A method as claimed in claim 43, further comprising processing the spectral responses to reduce random noise or unwanted signal that may be caused by instrumental responses using smoothing techniques.

53. A method as claimed in claim 43, further comprising processing the spectral responses to reduce random noise or unwanted signal that may be caused by instrumental responses using Savitsky-Golay smoothing.

54. A method as claimed in claim 43, further comprising processing the spectral responses to remove multiplicative effects.

55. A method as claimed in claim 43, further comprising processing the spectral responses using standard normal variance (SNV) analysis.

56. A method as claimed in claim 43, further comprising processing the spectral responses using multiplicative signal or scatter correction (MSC) analysis.

57. A method as claimed in claim 43, wherein the step of using the determined spectral responses to analyze the blood vessels comprises applying multivariate analysis for a qualification analysis, such as discrimination and classification, of the blood vessels.

58. A method as claimed in claim 57, wherein the multivariate analysis includes Principal Component Analysis.

59. A method as claimed in claim 57, wherein the multivariate analysis includes Principal Component Analysis combined with a statistical boundary, such as Mahalanobis distance.

60. A method as claimed in claim 57, wherein the multivariate analysis includes Principal Component Analysis combined with a residual analysis and a statistical boundary, such as Mahalanobis distance.

61. A method as claimed in claim 57, wherein the multivariate analysis includes Partial Least Squares Discriminant Analysis.

62. A method as claimed in claim 43, wherein the step of using the determined spectral responses to analyze the blood vessels comprises applying multivariate analysis for quantification of a state of the blood vessels.

63. A method as claimed in claim 62, wherein the multivariate analysis includes using Partial Least Squares analysis.

64. A method as claimed in claim 43, wherein the step of using the determined spectral responses to analyze the blood vessels comprises applying machine language learning for discrimination or classification of a state of the blood vessels.

65. A method as claimed in claim 64, wherein the machine language analysis includes using support vector machine analysis.

66. A method as claimed in claim 64, wherein the machine language analysis includes using artificial neural networks analysis.

67. A method as claimed in claim 43, wherein the step of processing the spectral responses comprises up-weighting the blood vessel responses.

68. A method as claimed in claim 43, wherein the step of processing the spectral responses comprises down-weighting the unwanted spectral signal.

69. A method as claimed in claim 43, wherein the step of processing the spectral responses comprises up-weighting the blood vessel responses and comprises down-weighting the unwanted spectral signal, in either order.

70. A method as claimed in claim 43, wherein the step of collecting the spectral responses comprise irradiating the blood vessels using a catheter.

71. A method as claimed in claim 43, wherein the unwanted spectral signal is generated at least in part by temperature fluctuation, heart motion, and/or catheter motion.

72. A method as claimed in claim 1, wherein the step of processing the spectral responses comprises processing the collected spectral responses, being a composite of intervening fluid and blood vessel walls, in an analyzer after detection of the collected spectral responses to remove or deemphasize the unwanted spectral signals.

* * * * *